United States Patent [19]
Adachi et al.

[11] Patent Number: 5,849,557
[45] Date of Patent: Dec. 15, 1998

[54] OXIDIZED PHOSPHOLIPID DEGRADING ENZYME AND GENE THEREOF

[75] Inventors: Hideki Adachi, Ibaraki; Masafumi Tsujimoto, Osaka; Keizo Inoue; Hiroyuki Arai, both of Tokyo, all of Japan

[73] Assignee: Suntory Limited, Osaka, Japan

[21] Appl. No.: 283,917

[22] Filed: Aug. 3, 1994

[30] Foreign Application Priority Data

Aug. 3, 1993 [JP] Japan .................................... 5-209943

[51] Int. Cl.⁶ ............................... C12N 9/20; C12N 9/18
[52] U.S. Cl. ............................................ 435/198; 435/197
[58] Field of Search ..................................... 435/197, 198

[56] References Cited

U.S. PATENT DOCUMENTS 5,466,595  11/1995  Jones et al. ........................... 435/240.2
5,519,003  5/1996  Mochley-Rosen et al. ............... 514/16

FOREIGN PATENT DOCUMENTS 638646  2/1995  European Pat. Off. .

OTHER PUBLICATIONS

Miwa et al. (1988) *J. Clin. Invest.*, 82, "Characterization of Serum Platelet–Activating Factor (PAF) Acetylhydrolase", pp. 1983–1991.
Yanoshita et al. (1988) *J. Biochem.*, 103(5), "Hydrolysis of Platelet Activating Factor and its Methylated Analogs by Acetylhydrolases", pp. 815–819.
Stafforini et al. (1993) *J. Biol. Chem.*, 268(6), "The Platelet–Activating Factor Acetylhydrolase from Human Erythrocytes", pp. 3857–3865.
Banerjee et al. (1994) *Science, 263,* "inhA, a Gene Encoding a Target for Isoniazid and Ethionamide in *Mycobacterium tuberculosis*", pp. 227–230.
Tjoelker et al. (1995) *Nature, 374,* "Anti–Inflammatory Properties of a Platelet–Activating Factor Acetylhydrolase", pp. 549–553.
Bazan (1995) *Nature, 374,* "A Signal Terminator", pp. 501–502.
Journal of Biological Chemistry, vol. 268, No. 25, pp. 18748–18753, Sep. 5, 1993, Mitsuharu Hattori, et al., "Purification and Characterization of Bovine Brain Platelet–Activating Factor Acetylhydrolase".
Nature, vol. 370, pp. 216–218, Jul. 21, 1994, Mitsuharu Hattori et al., "Miller–Dieker Lissencephaly Gene Encodes a Subunit of Brain Platelet–Activating Factor".
Nature, vol. 364, pp. 717–721, Aug. 19, 1993, Orly Reiner, et al., "Isolation of a Miller–Dieker Lissencephaly Gene Containing G Protein Beta–Subunit–Like Repeats".
The Journal of Biological Chemistry, vol. 269, No. 37, pp. 23150–23155, Sep. 16, 1994, Mitsuharu Hattori, et al., "The Catalytic Subunit of Bovine Brain Platelet–Activating Factor Acetylhydrolase is a Novel Type of Serine Esterase".
Biochemical and Biophysical Research Communications, vol. 214, No. 1, pp. 180–187, Sep. 05, 1995, Hideki Adachi, et al., CDNA Cloning of Human Cytosolic Platelet–Activating Factor Acetylhydrolase Gamma–Subunit and its MRNA Expression in Human Tissues.
The Journal of Biological Chemistry, vol. 270, No. 52, pp. 31345–31352, Dec. 29, 1995, Mitsuharu Hattori, et al., "Cloning and Expression of a CDNA Encoding the Beta–Subunit (30–KDA Subunit) of Bovine Brain Platelet–Activating Factor Acetylhydrolase".
Sevanian et al. (1981) *Lipids,* 16(11), "Metabolism of Epoxidized Phosphatidylcholine by Phospholipase $A_2$ and Epoxide Hydrolase", pp. 781–789.

*Primary Examiner*—Jon P. Weber
*Attorney, Agent, or Firm*—Oblon, Spivak, McClelland, Maier & Neustadt, P.C.

[57] ABSTRACT

An oxidized phospholipid degrading enzyme is provided, which plays an important role in the oxygen stress preventive mechanism in organisms. The enzyme hydrolyzes a 1-acyl-2-ω-carboxyfatty acid acyl-3-phosphatidylcholine as a substrate at the 2-ester bond thereof to form 1-acyl-2-lyso-3-phosphatidylcholine. The activity of the enzyme is slightly enhanced by 4 mM calcium chloride. The molecular mass of the enzyme is 95±5 kDa (by gel filtration). The enzyme is composed of three subunits whose molecular masses have been found to be 29 kDa, 30 kDa and 45 kDa, respectively, by SDS-polyacrylamide electrophoresis. A gene coding the enzyme is also provided. This gene is important for the synthesis of the enzyme by genetic engineering.

9 Claims, 6 Drawing Sheets

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 231 amino acids
        ( B ) TYPE: amino acid
        ( C ) STRANDEDNESS: unknown
        ( D ) TOPOLOGY: unknown ( i i ) MOLECULE TYPE: peptide (v i) ORIGINAL SOURCE:
  (A) ORGANISM: Bos taurus (x i) SEQUENCE DESCRIPTION: SEQ ID NO:1:

```
Ser  Gly  Asp  Glu  Asn  Pro  Ala  Ser  Lys  Pro  Thr  Pro  Val  Gln  Asp  Val
1                  5                        10                       15

Gln  Gly  Asp  Gly  Arg  Trp  Met  Ser  Leu  His  His  Arg  Phe  Val  Ala  Asp
                20                       25                       30

Ser  Lys  Asp  Lys  Glu  Pro  Glu  Val  Val  Phe  Ile  Gly  Asp  Ser  Leu  Val
            35                       40                       45

Gln  Leu  Met  His  Gln  Cys  Glu  Ile  Trp  Arg  Glu  Leu  Phe  Ser  Pro  Leu
        50                       55                       60

His  Ala  Leu  Asn  Phe  Gly  Ile  Gly  Gly  Asp  Ser  Thr  Gln  His  Val  Leu
65                       70                       75                       80

Trp  Arg  Leu  Glu  Asn  Gly  Glu  Leu  Glu  His  Ile  Arg  Pro  Lys  Ile  Val
                85                       90                       95

Val  Val  Trp  Val  Gly  Thr  Asn  Asn  His  Gly  His  Thr  Ala  Glu  Gln  Val
                100                      105                      110

Thr  Gly  Gly  Ile  Lys  Ala  Ile  Val  Gln  Leu  Val  Asn  Glu  Arg  Gln  Pro
            115                      120                      125

Gln  Ala  Arg  Val  Val  Val  Leu  Gly  Leu  Leu  Pro  Arg  Gly  Gln  His  Pro
        130                      135                      140

Thr  Gln  Leu  Arg  Glu  Lys  Asn  Arg  Arg  Val  Asn  Glu  Leu  Val  Arg  Ala
145                      150                      155                      160

Ala  Leu  Ala  Gly  His  Pro  Arg  Ala  His  Phe  Leu  Asp  Ala  Asp  Pro  Gly
                165                      170                      175

Phe  Val  His  Ser  Asp  Gly  Thr  Ile  Ser  His  His  Asp  Met  Tyr  Asp  Tyr
            180                      185                      190

Leu  His  Leu  Ser  Arg  Leu  Gly  Tyr  Thr  Pro  Val  Cys  Arg  Ala  Leu  His
        195                      200                      205

Ser  Leu  Leu  Leu  Arg  Leu  Leu  Thr  Gln  Asp  Gln  Gly  Gln  Gly  Gly  Ala
    210                      215                      220

Pro  Leu  Pro  Glu  Pro  Ser  Pro
225                      230
```

(2) INFORMATION FOR SEQ ID NO:2:

(i) SEQUENCE CHARACTERISTICS:
    (A) LENGTH: 112 amino acids
    (B) TYPE: amino acid
    (C) STRANDEDNESS: unknown
    (D) TOPOLOGY: unknown (ii) MOLECULE TYPE: peptide (v i) ORIGINAL SOURCE:
    (A) ORGANISM: Bos taurus (x i) SEQUENCE DESCRIPTION: SEQ ID NO:2:

```
Lys  Glu  Pro  Asp  Val  Leu  Phe  Val  Gly  Asp  Ser  Met  Val  Gln  Leu  Met
1                  5                        10                       15

Gln  Gln  Tyr  Glu  Ile  Trp  Arg  Glu  Leu  Phe  Ser  Pro  Leu  His  Ala  Leu
                20                       25                       30

Asn  Phe  Gly  Ile  Gly  Gly  Asp  Thr  Thr  Arg  His  Val  Leu  Trp  Arg  Leu
            35                       40                       45

Lys  Asn  Gly  Glu  Leu  Glu  Asn  Ile  Lys  Pro  Lys  Val  Ile  Val  Val  Trp
        50                       55                       60

Val  Gly  Thr  Asn  Asn  His  Glu  Asn  Thr  Ala  Glu  Glu  Val  Ala  Gly  Gly
65                       70                       75                       80
```

Ile Glu Ala Ile Val Gln Leu Ile Asn Thr Arg Gln Pro Gln Ala Lys
                    85                  90                  95

Ile Ile Val Leu Gly Leu Leu Pro Arg Gly Glu Lys Pro Asn Pro Leu
            100                 105                 110

(2) INFORMATION FOR SEQ ID NO:3:

(i) SEQUENCE CHARACTERISTICS:
      (A) LENGTH: 409 amino acids
      (B) TYPE: amino acid
      (C) STRANDEDNESS: unknown
      (D) TOPOLOGY: unknown (ii) MOLECULE TYPE: peptide (vi) ORIGINAL SOURCE:
      (A) ORGANISM: Bos taurus (xi) SEQUENCE DESCRIPTION: SEQ ID NO:3:

Val Leu Ser Gln Arg Gln Arg Asp Glu Leu Asn Arg Ala Ile Ala Asp
1               5                   10                  15

Tyr Leu Arg Ser Asn Gly Tyr Glu Glu Ala Tyr Ser Val Phe Lys Lys
            20                  25                  30

Glu Ala Glu Leu Asp Met Asn Glu Glu Leu Asp Lys Lys Tyr Ala Gly
            35                  40                  45

Leu Leu Glu Lys Lys Trp Thr Ser Val Ile Arg Leu Gln Lys Lys Val
50                  55                  60

Met Glu Leu Glu Ser Lys Leu Asn Glu Ala Lys Glu Glu Phe Thr Ser
65                  70                  75                  80

Gly Gly Pro Leu Gly Gln Lys Arg Asp Pro Lys Glu Trp Ile Pro Arg
            85                  90                  95

Pro Pro Glu Lys Tyr Ala Leu Ser Gly His Arg Ser Pro Val Thr Arg
            100                 105                 110

Val Ile Phe His Pro Val Phe Ser Val Met Val Ser Ala Ser Glu Asp
            115                 120                 125

Ala Thr Ile Lys Val Trp Asp Tyr Glu Thr Gly Asp Phe Glu Arg Thr
130                 135                 140

Leu Lys Gly His Thr Asp Ser Val Gln Asp Ile Ser Phe Asp His Ser
145                 150                 155                 160

Gly Lys Leu Leu Ala Ser Cys Ser Ala Asp Met Thr Ile Lys Leu Trp
            165                 170                 175

Asp Phe Gln Gly Phe Glu Cys Ile Arg Thr Met His Gly His Asp His
            180                 185                 190

Asn Val Ser Ser Val Ala Ile Met Pro Asn Gly Asp His Ile Val Ser
            195                 200                 205

Ala Ser Arg Asp Lys Thr Ile Lys Met Trp Glu Val Gln Thr Gly Tyr
210                 215                 220

Cys Val Lys Thr Phe Thr Gly His Arg Glu Trp Val Arg Met Val Arg
225                 230                 235                 240

Pro Asn Gln Asp Gly Thr Leu Ile Ala Ser Cys Ser Asn Asp Gln Thr
            245                 250                 255

Val Arg Val Trp Val Val Ala Thr Lys Glu Cys Lys Ala Glu Leu Arg
            260                 265                 270

Glu His Glu His Val Val Glu Cys Ile Ser Trp Ala Pro Glu Ser Ser
            275                 280                 285

Tyr Ser Ser Ile Ser Glu Ala Thr Gly Ser Glu Thr Lys Lys Ser Gly
290                 295                 300

```
Lys  Pro  Gly  Pro  Phe  Leu  Leu  Ser  Gly  Ser  Arg  Asp  Lys  Thr  Ile  Lys
305                      310                 315                      320

Met  Trp  Asp  Val  Ser  Thr  Gly  Met  Cys  Leu  Met  Thr  Leu  Val  Gly  His
                    325                 330                      335

Asp  Asn  Trp  Val  Arg  Gly  Val  Leu  Phe  His  Ser  Gly  Gly  Lys  Phe  Ile
                    340                 345                      350

Leu  Ser  Cys  Ala  Asp  Asp  Lys  Thr  Leu  Arg  Val  Trp  Asp  Tyr  Lys  Asn
          355                      360                      365

Lys  Arg  Cys  Met  Lys  Thr  Leu  Asn  Ala  His  Glu  His  Phe  Val  Thr  Ser
          370                 375                 380

Leu  Asp  Phe  His  Lys  Thr  Ala  Pro  Tyr  Val  Val  Thr  Gly  Ser  Val  Asp
385                      390                 395                           400

Gln  Thr  Val  Lys  Val  Trp  Glu  Cys  Arg
                    405
```

( 2 ) INFORMATION FOR SEQ ID NO:4:

( i ) SEQUENCE CHARACTERISTICS:
        ( A ) LENGTH: 820 base pairs
        ( B ) TYPE: nucleic acid
        ( C ) STRANDEDNESS: unknown
        ( D ) TOPOLOGY: unknown ( i i ) MOLECULE TYPE: cDNA ( v i ) ORIGINAL SOURCE:
        ( A ) ORGANISM: Bos taurus ( i x ) FEATURE:
        ( A ) NAME/KEY: CDS
        ( B ) LOCATION: 77..772

( x i ) SEQUENCE DESCRIPTION: SEQ ID NO:4:

```
TGGTTTCTTC  CCCCAGGACT  GGCGCTAGAT  TTCCCCCGCC  TACTCTCGGC  CTTCAGGAGC           60

GGAGGCGAGT  GGCAAG ATG  AGT  GGA  GAC  GAG  AAC  CCA  GCC  AGC  AAG  CCC        109
                   Met  Ser  Gly  Asp  Glu  Asn  Pro  Ala  Ser  Lys  Pro
                    1                 5                           10

ACG  CCA  GTG  CAG  GAC  GTG  CAG  GGT  GAC  GGG  CGC  TGG  ATG  TCC  CTG  CAC   157
Thr  Pro  Val  Gln  Asp  Val  Gln  Gly  Asp  Gly  Arg  Trp  Met  Ser  Leu  His
               15                      20                           25

CAT  CGG  TTC  GTA  GCC  GAC  AGC  AAA  GAT  AAG  GAA  CCC  GAA  GTC  GTC  TTC   205
His  Arg  Phe  Val  Ala  Asp  Ser  Lys  Asp  Lys  Glu  Pro  Glu  Val  Val  Phe
               30                      35                           40

ATC  GGT  GAC  TCC  TTG  GTC  CAG  CTG  ATG  CAC  CAG  TGC  GAG  ATC  TGG  CGG   253
Ile  Gly  Asp  Ser  Leu  Val  Gln  Leu  Met  His  Gln  Cys  Glu  Ile  Trp  Arg
     45                      50                      55

GAG  CTC  TTT  TCC  CCT  CTG  CAC  GCA  CTT  AAC  TTT  GGC  ATT  GGC  GGT  GAC   301
Glu  Leu  Phe  Ser  Pro  Leu  His  Ala  Leu  Asn  Phe  Gly  Ile  Gly  Gly  Asp
60                       65                      70                      75

AGC  ACA  CAG  CAT  GTG  CTG  TGG  CGT  CTG  GAG  AAT  GGA  GAG  CTG  GAA  CAC   349
Ser  Thr  Gln  His  Val  Leu  Trp  Arg  Leu  Glu  Asn  Gly  Glu  Leu  Glu  His
                    80                      85                           90

ATC  CGG  CCC  AAG  ATT  GTG  GTG  GTC  TGG  GTT  GGT  ACC  AAC  AAC  CAC  GGG   397
Ile  Arg  Pro  Lys  Ile  Val  Val  Val  Trp  Val  Gly  Thr  Asn  Asn  His  Gly
          95                      100                          105

CAC  ACT  GCA  GAG  CAG  GTG  ACT  GGG  GGC  ATC  AAG  GCC  ATA  GTG  CAG  CTG   445
His  Thr  Ala  Glu  Gln  Val  Thr  Gly  Gly  Ile  Lys  Ala  Ile  Val  Gln  Leu
          110                     115                          120

GTG  AAC  GAG  CGG  CAG  CCC  CAG  GCA  CGG  GTC  GTG  GTG  CTG  GGC  CTG  CTT   493
Val  Asn  Glu  Arg  Gln  Pro  Gln  Ala  Arg  Val  Val  Val  Leu  Gly  Leu  Leu
     125                     130                          135

CCT  CGG  GGC  CAG  CAC  CCC  ACC  CAA  CTT  CGA  GAG  AAA  AAC  CGA  CGG  GTG   541
```

| | | | | | | | | | | | | | | | |
|---|---|---|---|---|---|---|---|---|---|---|---|---|---|---|---|
|Pro|Arg|Gly|Gln|His|Pro|Thr|Gln|Leu|Arg|Glu|Lys|Asn|Arg|Arg|Val|
|140| | | |145| | | |150| | | | | | |155|

| | | | | | | | | | | | | | | | | |
|---|---|---|---|---|---|---|---|---|---|---|---|---|---|---|---|---|
|AAT|GAG|CTG|GTA|CGG|GCA|GCA|CTG|GCC|GGC|CAC|CCT|CGG|GCC|CAC|TTC|589|
|Asn|Glu|Leu|Val|Arg|Ala|Ala|Leu|Ala|Gly|His|Pro|Arg|Ala|His|Phe| |
| | | | |160| | | |165| | | | |170| | | |

| | | | | | | | | | | | | | | | | |
|---|---|---|---|---|---|---|---|---|---|---|---|---|---|---|---|---|
|CTG|GAC|GCA|GAC|CCT|GGC|TTT|GTG|CAC|TCA|GAT|GGT|ACC|ATC|AGC|CAC|637|
|Leu|Asp|Ala|Asp|Pro|Gly|Phe|Val|His|Ser|Asp|Gly|Thr|Ile|Ser|His| |
| | | |175| | | |180| | | |185| | | | | |

| | | | | | | | | | | | | | | | | |
|---|---|---|---|---|---|---|---|---|---|---|---|---|---|---|---|---|
|CAT|GAC|ATG|TAC|GAT|TAC|CTG|CAC|CTG|AGC|CGT|CTG|GGG|TAC|ACA|CCT|685|
|His|Asp|Met|Tyr|Asp|Tyr|Leu|His|Leu|Ser|Arg|Leu|Gly|Tyr|Thr|Pro| |
| | |190| | | |195| | | |200| | | | | | |

| | | | | | | | | | | | | | | | | |
|---|---|---|---|---|---|---|---|---|---|---|---|---|---|---|---|---|
|GTT|TGC|CGG|GCC|CTG|CAC|TCC|TTG|CTT|CTG|CGT|CTG|CTA|ACC|CAA|GAC|733|
|Val|Cys|Arg|Ala|Leu|His|Ser|Leu|Leu|Leu|Arg|Leu|Leu|Thr|Gln|Asp| |
| |205| | | | |210| | | |215| | | | | | |

| | | | | | | | | | | | | | |
|---|---|---|---|---|---|---|---|---|---|---|---|---|---|
|CAG|GGA|CAG|GGT|GGT|GCC|CCC|CTG|CCG|GAA|CCC|AGC|CCC|TAAGCATCTG|782|
|Gln|Gly|Gln|Gly|Gly|Ala|Pro|Leu|Pro|Glu|Pro|Ser|Pro| | |
|220| | | | |225| | | |230| | | | | |

TCTTCCTACA ACATTAAATT TTCATTTTC AGTCAAAA         820

( 2 ) INFORMATION FOR SEQ ID NO:5:

( i ) SEQUENCE CHARACTERISTICS:
  ( A ) LENGTH: 232 amino acids
  ( B ) TYPE: amino acid
  ( D ) TOPOLOGY: linear ( i i ) MOLECULE TYPE: protein ( x i ) SEQUENCE DESCRIPTION: SEQ ID NO:5:

| | | | | | | | | | | | | | | |
|---|---|---|---|---|---|---|---|---|---|---|---|---|---|---|
|Met|Ser|Gly|Asp|Glu|Asn|Pro|Ala|Ser|Lys|Pro|Thr|Pro|Val|Gln|Asp|
|1| | | |5| | | |10| | | | |15| |

| | | | | | | | | | | | | | | |
|---|---|---|---|---|---|---|---|---|---|---|---|---|---|---|
|Val|Gln|Gly|Asp|Gly|Arg|Trp|Met|Ser|Leu|His|His|Arg|Phe|Val|Ala|
| | | |20| | | |25| | | | |30| | |

| | | | | | | | | | | | | | | |
|---|---|---|---|---|---|---|---|---|---|---|---|---|---|---|
|Asp|Ser|Lys|Asp|Lys|Glu|Pro|Glu|Val|Val|Phe|Ile|Gly|Asp|Ser|Leu|
| | |35| | | |40| | | | |45| | | |

| | | | | | | | | | | | | | | |
|---|---|---|---|---|---|---|---|---|---|---|---|---|---|---|
|Val|Gln|Leu|Met|His|Gln|Cys|Glu|Ile|Trp|Arg|Glu|Leu|Phe|Ser|Pro|
| |50| | | | |55| | | |60| | | | |

| | | | | | | | | | | | | | | |
|---|---|---|---|---|---|---|---|---|---|---|---|---|---|---|
|Leu|His|Ala|Leu|Asn|Phe|Gly|Ile|Gly|Gly|Asp|Ser|Thr|Gln|His|Val|
|65| | | |70| | | |75| | | | | | |80|

| | | | | | | | | | | | | | | |
|---|---|---|---|---|---|---|---|---|---|---|---|---|---|---|
|Leu|Trp|Arg|Leu|Glu|Asn|Gly|Glu|Leu|Glu|His|Ile|Arg|Pro|Lys|Ile|
| | | | |85| | | |90| | | | |95| |

| | | | | | | | | | | | | | | |
|---|---|---|---|---|---|---|---|---|---|---|---|---|---|---|
|Val|Val|Val|Trp|Val|Gly|Thr|Asn|Asn|His|Gly|His|Thr|Ala|Glu|Gln|
| | | |100| | | |105| | | | |110| | |

| | | | | | | | | | | | | | | |
|---|---|---|---|---|---|---|---|---|---|---|---|---|---|---|
|Val|Thr|Gly|Gly|Ile|Lys|Ala|Ile|Val|Gln|Leu|Val|Asn|Glu|Arg|Gln|
| | |115| | | |120| | | | |125| | | |

| | | | | | | | | | | | | | | |
|---|---|---|---|---|---|---|---|---|---|---|---|---|---|---|
|Pro|Gln|Ala|Arg|Val|Val|Val|Leu|Gly|Leu|Leu|Pro|Arg|Gly|Gln|His|
| |130| | | | |135| | | |140| | | | |

| | | | | | | | | | | | | | | |
|---|---|---|---|---|---|---|---|---|---|---|---|---|---|---|
|Pro|Thr|Gln|Leu|Arg|Glu|Lys|Asn|Arg|Arg|Val|Asn|Glu|Leu|Val|Arg|
|145| | | |150| | | |155| | | | | | |160|

| | | | | | | | | | | | | | | |
|---|---|---|---|---|---|---|---|---|---|---|---|---|---|---|
|Ala|Ala|Leu|Ala|Gly|His|Pro|Arg|Ala|His|Phe|Leu|Asp|Ala|Asp|Pro|
| | | |165| | | |170| | | | |175| | |

| | | | | | | | | | | | | | | |
|---|---|---|---|---|---|---|---|---|---|---|---|---|---|---|
|Gly|Phe|Val|His|Ser|Asp|Gly|Thr|Ile|Ser|His|His|Asp|Met|Tyr|Asp|
| | |180| | | |185| | | | |190| | | |

| | | | | | | | | | | | | | | |
|---|---|---|---|---|---|---|---|---|---|---|---|---|---|---|
|Tyr|Leu|His|Leu|Ser|Arg|Leu|Gly|Tyr|Thr|Pro|Val|Cys|Arg|Ala|Leu|
| |195| | | |200| | | | |205| | | | |

| | | | | | | | | | | | | |
|---|---|---|---|---|---|---|---|---|---|---|---|---|
|His|Ser|Leu|Leu|Leu|Arg|Leu|Leu|Thr|Gln|Asp|Gln|Gly|Gln|Gly|Gly|
|210| | | |215| | | |220| | | | | | | |

| | | | | | | |
|---|---|---|---|---|---|---|
|Ala|Pro|Leu|Pro|Glu|Pro|Ser|Pro|

(2) INFORMATION FOR SEQ ID NO:6:

(i) SEQUENCE CHARACTERISTICS:
        (A) LENGTH: 336 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Bos taurus (ix) FEATURE:
        (A) NAME/KEY: CDS
        (B) LOCATION: 1..336

(xi) SEQUENCE DESCRIPTION: SEQ ID NO:6:

```
AAG  GAG  CCG  GAT  GTC  CTG  TTC  GTG  GGG  GAC  TCC  ATG  GTA  CAG  TTG  ATG      48
Lys  Glu  Pro  Asp  Val  Leu  Phe  Val  Gly  Asp  Ser  Met  Val  Gln  Leu  Met
 1                  5                        10                      15

CAG  CAG  TAT  GAG  ATA  TGG  CGA  GAG  CTT  TTT  TCT  CCA  CTT  CAT  GCA  CTG      96
Gln  Gln  Tyr  Glu  Ile  Trp  Arg  Glu  Leu  Phe  Ser  Pro  Leu  His  Ala  Leu
                20                        25                      30

AAT  TTT  GGA  ATT  GGG  GGA  GAT  ACA  ACA  AGA  CAT  GTT  TTA  TGG  AGA  CTT     144
Asn  Phe  Gly  Ile  Gly  Gly  Asp  Thr  Thr  Arg  His  Val  Leu  Trp  Arg  Leu
           35                        40                      45

AAG  AAT  GGA  GAA  CTG  GAG  AAT  ATT  AAA  CCT  AAG  GTC  ATC  GTT  GTC  TGG     192
Lys  Asn  Gly  Glu  Leu  Glu  Asn  Ile  Lys  Pro  Lys  Val  Ile  Val  Val  Trp
      50                        55                      60

GTA  GGA  ACA  AAC  AAC  CAT  GAA  AAT  ACA  GCA  GAG  GAA  GTA  GCA  GGT  GGA     240
Val  Gly  Thr  Asn  Asn  His  Glu  Asn  Thr  Ala  Glu  Glu  Val  Ala  Gly  Gly
 65                      70                      75                      80

ATC  GAG  GCC  ATC  GTA  CAG  CTT  ATC  AAC  ACA  AGG  CAG  CCA  CAG  GCC  AAA     288
Ile  Glu  Ala  Ile  Val  Gln  Leu  Ile  Asn  Thr  Arg  Gln  Pro  Gln  Ala  Lys
                     85                       90                      95

ATC  ATT  GTA  TTG  GGT  TTG  TTA  CCT  CGA  GGT  GAG  AAG  CCC  AAC  CCT  CTC     336
Ile  Ile  Val  Leu  Gly  Leu  Leu  Pro  Arg  Gly  Glu  Lys  Pro  Asn  Pro  Leu
               100                      105                     110
```

(2) INFORMATION FOR SEQ ID NO:7:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO:7:

```
Lys  Glu  Pro  Asp  Val  Leu  Phe  Val  Gly  Asp  Ser  Met  Val  Gln  Leu  Met
 1                  5                        10                      15

Gln  Gln  Tyr  Glu  Ile  Trp  Arg  Glu  Leu  Phe  Ser  Pro  Leu  His  Ala  Leu
                20                        25                      30

Asn  Phe  Gly  Ile  Gly  Gly  Asp  Thr  Thr  Arg  His  Val  Leu  Trp  Arg  Leu
           35                        40                      45

Lys  Asn  Gly  Glu  Leu  Glu  Asn  Ile  Lys  Pro  Lys  Val  Ile  Val  Val  Trp
      50                        55                      60

Val  Gly  Thr  Asn  Asn  His  Glu  Asn  Thr  Ala  Glu  Glu  Val  Ala  Gly  Gly
 65                      70                      75                      80

Ile  Glu  Ala  Ile  Val  Gln  Leu  Ile  Asn  Thr  Arg  Gln  Pro  Gln  Ala  Lys
                     85                       90                      95
```

```
Ile Ile Val Leu Gly Leu Leu Pro Arg Gly Glu Lys Pro Asn Pro Leu
        100                 105                 110
```

(2) INFORMATION FOR SEQ ID NO:8:

(i) SEQUENCE CHARACTERISTICS:
        (A) LENGTH: 2085 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Bos taurus (ix) FEATURE:
        (A) NAME/KEY: CDS
        (B) LOCATION: 844..2073

(xi) SEQUENCE DESCRIPTION: SEQ ID NO:8:

```
GCGGCCGCGA  CGGCCGTTGA  GTGAGAGACA  CGGGAGGAGG  GGGGGACAGG  CCGGGTAGGG      60

CGCTGCCCTC  GCTCCCCTCC  TCCCTGGCCC  GGGTTCTGGG  GGTGCCAGGG  CCGCCGCGGC     120

TCCACCCGCG  GCCTTCCCCG  GGAAGGGATC  GCCTTCCTCC  CTTGGTGACT  TAGCAAGAAA     180

AGTATTCTTG  GGTAGGAAGG  GCGTGGGGAG  CAGGTCCCTC  TCAGATCTTG  GGGAGAGGGT     240

TCGGCTCTCC  TCTCCCTGTC  CGCGGGAGAG  AAGCTCCGCA  GTCCCCACCC  CGCCCCGCGG     300

CTGGCGCTCA  GGGACCGGGC  TCAAGCCTCC  TCGGCACTGT  CCACCGGCCT  GCAGGCGTTC     360

TGTCCCCCAC  CTGTCCTTAG  GATGGAGTTG  ACCTGAGAAG  GATGGTCCAG  CCTTTCCCTG     420

GCCCCCCTAT  GCGGTGGTTC  AGCCCCTGCA  CCCACTGAGG  AGGAGCGGCC  TGACCCCACC     480

GAACCATCCG  CAGCATCCAC  CCACCAAATC  CGGCAGGATT  TTCTTTTCTG  CCGTCGGCTC     540

CTTCAACGGG  AGCTGCCTTT  TGACGTTGTA  ACACTGAGCT  TCGAGGCCCT  CAGCCATTCT     600

CCTTCGAATC  TCCCCACTCG  TATAGGAAAC  GCAGTGCCTG  CCTTAACCTC  CCAGGTGGAA     660

TGAACCTTAC  TTGTTGAATA  TCTCCTGGTT  ACACGTTGGA  TTCACTTGTG  AAAGAATCAT     720

TTTCCCCTGC  GTGAAAGCCA  CTTAGTGGCT  TATTAATTAT  AAATCCAGGG  GTTGCAAAGC     780

TTTTTGATTT  TCCAGAGGAG  GGACATAACC  ACTATATCGA  ATAAGCTTGA  TATTACAGCC     840

AAA ATG GTG CTG TCC CAG AGA CAA CGA GAT GAA CTA AAT CGA GCT ATA           888
    Met Val Leu Ser Gln Arg Gln Arg Asp Glu Leu Asn Arg Ala Ile
     1               5                  10                  15

GCA GAT TAT CTT CGT TCA AAT GGC TAC GAA GAA GCA TAT TCA GTT TTT           936
Ala Asp Tyr Leu Arg Ser Asn Gly Tyr Glu Glu Ala Tyr Ser Val Phe
             20                  25                  30

AAA AAG GAA GCT GAA TTA GAT ATG AAT GAA GAA TTA GAT AAG AAA TAT           984
Lys Lys Glu Ala Glu Leu Asp Met Asn Glu Glu Leu Asp Lys Lys Tyr
         35                  40                  45

GCT GGT CTT TTG GAA AAA AAA TGG ACA TCT GTT ATT AGA TTA CAA AAG          1032
Ala Gly Leu Leu Glu Lys Lys Trp Thr Ser Val Ile Arg Leu Gln Lys
     50                  55                  60

AAG GTT ATG GAA TTA GAA TCA AAG TTA AAT GAA GCA AAA GAA GAA TTT          1080
Lys Val Met Glu Leu Glu Ser Lys Leu Asn Glu Ala Lys Glu Glu Phe
 65                  70                  75

ACG TCG GGT GGA CCT CTT GGT CAG AAA AGA GAC CCA AAA GAA TGG ATT          1128
Thr Ser Gly Gly Pro Leu Gly Gln Lys Arg Asp Pro Lys Glu Trp Ile
 80                  85                  90                  95

CCC CGT CCA CCA GAA AAA TAT GCA TTG AGT GGT CAT AGG AGT CCA GTC          1176
Pro Arg Pro Pro Glu Lys Tyr Ala Leu Ser Gly His Arg Ser Pro Val
                100                 105                 110

ACT CGA GTC ATT TTC CAT CCT GTG TTC AGT GTT ATG GTC TCT GCT TCA          1224
```

| | | | | | | | | | | | | | | | |
|---|---|---|---|---|---|---|---|---|---|---|---|---|---|---|---|
| Thr | Arg | Val | Ile 115 | Phe | His | Pro | Val 120 | Phe | Ser | Val | Met | Ser 125 | Ala | Ser | |
| GAG | GAT | GCT | ACA | ATT | AAG | GTG | TGG | GAT | TAT | GAG | ACT | GGA | GAT | TTT | GAA | 1272 |
| Glu | Asp | Ala 130 | Thr | Ile | Lys | Val | Trp 135 | Asp | Tyr | Glu | Thr | Gly 140 | Asp | Phe | Glu |
| CGA | ACT | CTT | AAG | GGG | CAT | ACA | GAC | TCT | GTA | CAG | GAT | ATT | TCA | TTC | GAC | 1320 |
| Arg | Thr 145 | Leu | Lys | Gly | His | Thr 150 | Asp | Ser | Val | Gln | Asp 155 | Ile | Ser | Phe | Asp |
| CAC | AGT | GGC | AAG | CTT | CTG | GCT | TCA | TGT | TCT | GCA | GAT | ATG | ACC | ATT | AAG | 1368 |
| His 160 | Ser | Gly | Lys | Leu | Leu 165 | Ala | Ser | Cys | Ser | Ala 170 | Asp | Met | Thr | Ile | Lys 175 |
| CTA | TGG | GAT | TTT | CAG | GGC | TTT | GAA | TGC | ATC | AGA | ACC | ATG | CAT | GGC | CAT | 1416 |
| Leu | Trp | Asp | Phe | Gln 180 | Gly | Phe | Glu | Cys | Ile 185 | Arg | Thr | Met | His | Gly 190 | His |
| GAC | CAC | AAT | GTT | TCT | TCA | GTA | GCC | ATC | ATG | CCC | AAT | GGA | GAT | CAT | ATA | 1464 |
| Asp | His | Asn | Val 195 | Ser | Ser | Val | Ala | Ile 200 | Met | Pro | Asn | Gly | Asp 205 | His | Ile |
| GTG | TCT | GCC | TCA | AGG | GAT | AAA | ACT | ATA | AAA | ATG | TGG | GAA | GTG | CAA | ACT | 1512 |
| Val | Ser | Ala 210 | Ser | Arg | Asp | Lys | Thr 215 | Ile | Lys | Met | Trp | Glu 220 | Val | Gln | Thr |
| GGC | TAC | TGT | GTG | AAG | ACA | TTC | ACA | GGA | CAC | AGA | GAA | TGG | GTA | CGT | ATG | 1560 |
| Gly | Tyr 225 | Cys | Val | Lys | Thr | Phe 230 | Thr | Gly | His | Arg | Glu 235 | Trp | Val | Arg | Met |
| GTG | CGG | CCA | AAT | CAA | GAC | GGC | ACT | CTG | ATA | GCC | AGC | TGT | TCC | AAT | GAC | 1608 |
| Val 240 | Arg | Pro | Asn | Gln | Asp 245 | Gly | Thr | Leu | Ile | Ala 250 | Ser | Cys | Ser | Asn | Asp 255 |
| CAG | ACT | GTG | CGT | GTA | TGG | GTC | GTA | GCA | ACA | AAG | GAA | TGC | AAG | GCT | GAG | 1656 |
| Gln | Thr | Val | Arg | Val 260 | Trp | Val | Val | Ala | Thr 265 | Lys | Glu | Cys | Lys | Ala 270 | Glu |
| CTT | CGA | GAA | CAT | GAG | CAT | GTG | GTA | GAA | TGC | ATT | TCC | TGG | GCT | CCT | GAA | 1704 |
| Leu | Arg | Glu | His 275 | Glu | His | Val | Val | Glu 280 | Cys | Ile | Ser | Trp | Ala 285 | Pro | Glu |
| AGC | TCA | TAT | TCT | TCC | ATC | TCT | GAA | GCA | ACA | GGA | TCT | GAG | ACT | AAA | AAA | 1752 |
| Ser | Ser | Tyr 290 | Ser | Ser | Ile | Ser | Glu 295 | Ala | Thr | Gly | Ser | Glu 300 | Thr | Lys | Lys |
| AGT | GGC | AAA | CCT | GGG | CCA | TTC | TTA | CTG | TCC | GGA | TCC | AGG | GAC | AAG | ACT | 1800 |
| Ser | Gly | Lys 305 | Pro | Gly | Pro | Phe | Leu 310 | Leu | Ser | Gly | Ser | Arg 315 | Asp | Lys | Thr |
| ATC | AAG | ATG | TGG | GAT | GTC | AGT | ACT | GGC | ATG | TGC | CTT | ATG | ACC | CTG | GTG | 1848 |
| Ile 320 | Lys | Met | Trp | Asp | Val 325 | Ser | Thr | Gly | Met | Cys 330 | Leu | Met | Thr | Leu | Val 335 |
| GGT | CAT | GAT | AAC | TGG | GTA | CGT | GGA | GTT | CTG | TTC | CAT | TCT | GGG | GGG | AAG | 1896 |
| Gly | His | Asp | Asn | Trp 340 | Val | Arg | Gly | Val | Leu 345 | Phe | His | Ser | Gly | Gly 350 | Lys |
| TTT | ATT | TTG | AGT | TGC | GCT | GAT | GAC | AAG | ACC | CTG | CGC | GTG | TGG | GAT | TAC | 1944 |
| Phe | Ile | Leu | Ser 355 | Cys | Ala | Asp | Asp | Lys 360 | Thr | Leu | Arg | Val | Trp 365 | Asp | Tyr |
| AAG | AAC | AAG | CGA | TGC | ATG | AAG | ACC | CTC | AAT | GCG | CAT | GAA | CAC | TTT | GTT | 1992 |
| Lys | Asn | Lys | Arg 370 | Cys | Met | Lys | Thr | Leu 375 | Asn | Ala | His | Glu | His 380 | Phe | Val |
| ACC | TCC | TTG | GAT | TTC | CAT | AAG | ACG | GCC | CCA | TAT | GTG | GTT | ACT | GGC | AGT | 2040 |
| Thr | Ser | Leu | Asp | Phe 385 | His | Lys | Thr | Ala | Pro 390 | Tyr | Val | Val | Thr | Gly 395 | Ser |
| GTA | GAT | CAA | ACA | GTA | AAG | GTG | TGG | GAG | TGT | CGT | TGATTGAGTC | TC | | | | 2085 |
| Val 400 | Asp | Gln | Thr | Val | Lys 405 | Val | Trp | Glu | Cys | Arg 410 | | | | | |

( 2 ) INFORMATION FOR SEQ ID NO:9:

( i ) SEQUENCE CHARACTERISTICS:
        ( A ) LENGTH: 410 amino acids (B) TYPE: amino acid
(D) TOPOLOGY: linear (ii) MOLECULE TYPE: protein (xi) SEQUENCE DESCRIPTION: SEQ ID NO:9:

```
Met Val Leu Ser Gln Arg Gln Arg Asp Glu Leu Asn Arg Ala Ile Ala
 1               5                  10                  15
Asp Tyr Leu Arg Ser Asn Gly Tyr Glu Ala Tyr Ser Val Phe Lys
            20                  25                  30
Lys Glu Ala Glu Leu Asp Met Asn Glu Glu Leu Asp Lys Lys Tyr Ala
            35                  40                  45
Gly Leu Leu Glu Lys Lys Trp Thr Ser Val Ile Arg Leu Gln Lys Lys
        50                  55                  60
Val Met Glu Leu Glu Ser Lys Leu Asn Glu Ala Lys Glu Glu Phe Thr
65                  70                  75                  80
Ser Gly Gly Pro Leu Gly Gln Lys Arg Asp Pro Lys Glu Trp Ile Pro
                85                  90                  95
Arg Pro Pro Glu Lys Tyr Ala Leu Ser Gly His Arg Ser Pro Val Thr
            100                 105                 110
Arg Val Ile Phe His Pro Val Phe Ser Val Met Val Ser Ala Ser Glu
            115                 120                 125
Asp Ala Thr Ile Lys Val Trp Asp Tyr Glu Thr Gly Asp Phe Glu Arg
    130                 135                 140
Thr Leu Lys Gly His Thr Asp Ser Val Gln Asp Ile Ser Phe Asp His
145                 150                 155                 160
Ser Gly Lys Leu Leu Ala Ser Cys Ser Ala Asp Met Thr Ile Lys Leu
                165                 170                 175
Trp Asp Phe Gln Gly Phe Glu Cys Ile Arg Thr Met His Gly His Asp
            180                 185                 190
His Asn Val Ser Ser Val Ala Ile Met Pro Asn Gly Asp His Ile Val
        195                 200                 205
Ser Ala Ser Arg Asp Lys Thr Ile Lys Met Trp Glu Val Gln Thr Gly
    210                 215                 220
Tyr Cys Val Lys Thr Phe Thr Gly His Arg Glu Trp Val Arg Met Val
225                 230                 235                 240
Arg Pro Asn Gln Asp Gly Thr Leu Ile Ala Ser Cys Ser Asn Asp Gln
                245                 250                 255
Thr Val Arg Val Trp Val Val Ala Thr Lys Glu Cys Lys Ala Glu Leu
            260                 265                 270
Arg Glu His Glu His Val Val Glu Cys Ile Ser Trp Ala Pro Glu Ser
            275                 280                 285
Ser Tyr Ser Ser Ile Ser Glu Ala Thr Gly Ser Glu Thr Lys Lys Ser
    290                 295                 300
Gly Lys Pro Gly Pro Phe Leu Leu Ser Gly Ser Arg Asp Lys Thr Ile
305                 310                 315                 320
Lys Met Trp Asp Val Ser Thr Gly Met Cys Leu Met Thr Leu Val Gly
                325                 330                 335
His Asp Asn Trp Val Arg Gly Val Leu Phe His Ser Gly Lys Phe
            340                 345                 350
Ile Leu Ser Cys Ala Asp Asp Lys Thr Leu Arg Val Trp Asp Tyr Lys
        355                 360                 365
Asn Lys Arg Cys Met Lys Thr Leu Asn Ala His Glu His Phe Val Thr
    370                 375                 380
Ser Leu Asp Phe His Lys Thr Ala Pro Tyr Val Val Thr Gly Ser Val
```

```
385                 390                 395                 400
Asp Gln Thr Val Lys Val Trp Glu Cys Arg
                405                 410
```

( 2 ) INFORMATION FOR SEQ ID NO:10:

( i ) SEQUENCE CHARACTERISTICS:
        ( A ) LENGTH: 16 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:10:

```
Ile Val Val Val Trp Val Gly Thr Asn Asn His Gly His Thr Ala Glu
1               5                   10                  15
```

( 2 ) INFORMATION FOR SEQ ID NO:11:

( i ) SEQUENCE CHARACTERISTICS:
        ( A ) LENGTH: 27 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:11:

```
Ala Ile Val Gln Leu Val Asn Glu Arg Gln Pro Gln Ala Arg Val Val
1               5                   10                  15

Val Leu Gly Leu Leu Pro Arg Gly Gln His Pro
                20                  25
```

( 2 ) INFORMATION FOR SEQ ID NO:12:

( i ) SEQUENCE CHARACTERISTICS:
        ( A ) LENGTH: 37 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:12:

```
Asp Lys Glu Pro Glu Val Val Phe Ile Gly Asp Ser Leu Val Gln Leu
1               5                   10                  15

Met His Gln Cys Glu Ile Trp Arg Glu Leu Phe Ser Pro Leu His Ala
                20                  25                  30

Leu Asn Phe Gly Ile
                35
```

( 2 ) INFORMATION FOR SEQ ID NO:13:

( i ) SEQUENCE CHARACTERISTICS:
        ( A ) LENGTH: 16 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:13:

```
Asp Lys Glu Pro Asp Val Leu Phe Val Gly Asp Ser Met Val Gln Leu
1               5                   10                  15
```

( 2 ) INFORMATION FOR SEQ ID NO:14:

( i ) SEQUENCE CHARACTERISTICS:
   ( A ) LENGTH: 18 amino acids
   ( B ) TYPE: amino acid
   ( C ) STRANDEDNESS: unknown
   ( D ) TOPOLOGY: unknown ( i i ) MOLECULE TYPE: peptide ( x i ) SEQUENCE DESCRIPTION: SEQ ID NO:14:

```
Ile  Ile  Val  Leu  Gly  Leu  Leu  Pro  Arg  Gly  Glu  Lys  Pro  Asn  Pro  Leu
1              5                        10                       15
Arg  Lys
```

( 2 ) INFORMATION FOR SEQ ID NO:15:

( i ) SEQUENCE CHARACTERISTICS:
      ( A ) LENGTH: 30 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:15:

```
Leu  Ala  Asn  Val  Gln  Leu  Leu  Asp  Thr  Xaa  Gly  Gly  Phe  Val  His  Ser
1              5                        10                       15
Asp  Gly  Ala  Ile  Ser  Cys  His  Asp  Met  Phe  Asp  Phe  Leu  His
               20             25                       30
```

( 2 ) INFORMATION FOR SEQ ID NO:16:

( i ) SEQUENCE CHARACTERISTICS:
      ( A ) LENGTH: 27 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:16:

```
Val  Leu  Ser  Gln  Arg  Gln  Arg  Asp  Glu  Leu  Asn  Arg  Ala  Ile  Ala  Asp
1              5                        10                       15
Tyr  Leu  Arg  Ser  Asn  Gly  Tyr  Glu  Glu  Ala  Tyr
               20                  25
```

( 2 ) INFORMATION FOR SEQ ID NO:17:

( i ) SEQUENCE CHARACTERISTICS:
      ( A ) LENGTH: 19 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:17:

```
Thr  Phe  Thr  Gly  His  Arg  Glu  Trp  Val  Arg  Met  Val  Arg  Pro  Asn  Gln
1              5                        10                       15
Asp  Gly  Thr
```

( 2 ) INFORMATION FOR SEQ ID NO:18:

( i ) SEQUENCE CHARACTERISTICS:
      ( A ) LENGTH: 16 amino acids
      ( B ) TYPE: amino acid
      ( C ) STRANDEDNESS: unknown
      ( D ) TOPOLOGY: unknown (i i) MOLECULE TYPE: peptide (x i) SEQUENCE DESCRIPTION: SEQ ID NO:18:

Thr Leu Asn Ala His Glu His Phe Val Thr Ser Leu Asp Phe His Lys
1               5                   10                  15

(2) INFORMATION FOR SEQ ID NO:19:

(i) SEQUENCE CHARACTERISTICS:
(A) LENGTH: 5 amino acids
(B) TYPE: amino acid
(C) STRANDEDNESS: unknown
(D) TOPOLOGY: unknown (i i) MOLECULE TYPE: peptide (x i) SEQUENCE DESCRIPTION: SEQ ID NO:19:

Val Trp Glu Cys Arg
1               5

(2) INFORMATION FOR SEQ ID NO:20:

(i) SEQUENCE CHARACTERISTICS:
(A) LENGTH: 17 base pairs
(B) TYPE: nucleic acid
(C) STRANDEDNESS: unknown
(D) TOPOLOGY: unknown (i i) MOLECULE TYPE: Other nucleic acid (x i) SEQUENCE DESCRIPTION: SEQ ID NO:20:

GGYTGNCKYT CRTTNAC                                                                  17

(2) INFORMATION FOR SEQ ID NO:21:

(i) SEQUENCE CHARACTERISTICS:
(A) LENGTH: 17 base pairs
(B) TYPE: nucleic acid
(C) STRANDEDNESS: unknown
(D) TOPOLOGY: unknown (i i) MOLECULE TYPE: Other nucleic acid (x i) SEQUENCE DESCRIPTION: SEQ ID NO:21:

CAYCARTGYG ARATHTG                                                                  17

(2) INFORMATION FOR SEQ ID NO:22:

(i) SEQUENCE CHARACTERISTICS:
(A) LENGTH: 18 base pairs
(B) TYPE: nucleic acid
(C) STRANDEDNESS: unknown
(D) TOPOLOGY: unknown (i i) MOLECULE TYPE: Other nucleic acid (x i) SEQUENCE DESCRIPTION: SEQ ID NO:22:

ATGTGCTGTG GCGTCTGG                                                                 18

(2) INFORMATION FOR SEQ ID NO:23:

(i) SEQUENCE CHARACTERISTICS:
(A) LENGTH: 18 base pairs
(B) TYPE: nucleic acid
(C) STRANDEDNESS: unknown
(D) TOPOLOGY: unknown (i i) MOLECULE TYPE: Other nucleic acid ( x i ) SEQUENCE DESCRIPTION: SEQ ID NO:23:

AGTGTGCCCG TGGTTGTT                                                                              18

( 2 ) INFORMATION FOR SEQ ID NO:24:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: Other nucleic acid ( x i ) SEQUENCE DESCRIPTION: SEQ ID NO:24:

AARGARCCCN GAYGTNYT                                                                              18

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: Other nucleic acid ( x i ) SEQUENCE DESCRIPTION: SEQ ID NO:25:

NARNGGRTTN GGYTTKT                                                                               17

( 2 ) INFORMATION FOR SEQ ID NO:26:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: Other nucleic acid ( x i ) SEQUENCE DESCRIPTION: SEQ ID NO:26:

GGNTAYGARG ARGCNTA                                                                               17

( 2 ) INFORMATION FOR SEQ ID NO:27:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: Other nucleic acid ( x i ) SEQUENCE DESCRIPTION: SEQ ID NO:27:

TGRTTNGGNC KNACCAT                                                                               17

( 2 ) INFORMATION FOR SEQ ID NO:28:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: Other nucleic acid ( x i ) SEQUENCE DESCRIPTION: SEQ ID NO:28:

AAGAGACCCA AAAGAATG                                                                              18

-continued ( 2 ) INFORMATION FOR SEQ ID NO:29:

( i ) SEQUENCE CHARACTERISTICS:
( A ) LENGTH: 18 base pairs
( B ) TYPE: nucleic acid
( C ) STRANDEDNESS: unknown
( D ) TOPOLOGY: unknown ( i i ) MOLECULE TYPE: Other nucleic acid ( x i ) SEQUENCE DESCRIPTION: SEQ ID NO:29:

GCACTTCCCA CATTTTTA                     18

( 2 ) INFORMATION FOR SEQ ID NO:30:

( i ) SEQUENCE CHARACTERISTICS:
( A ) LENGTH: 17 base pairs
( B ) TYPE: nucleic acid
( C ) STRANDEDNESS: unknown
( D ) TOPOLOGY: unknown ( i i ) MOLECULE TYPE: Other nucleic acid ( x i ) SEQUENCE DESCRIPTION: SEQ ID NO:30:

CAGGAAACAG CTATGAC                     17

( 2 ) INFORMATION FOR SEQ ID NO:31:

( i ) SEQUENCE CHARACTERISTICS:
( A ) LENGTH: 16 base pairs
( B ) TYPE: nucleic acid
( C ) STRANDEDNESS: unknown
( D ) TOPOLOGY: unknown ( i i ) MOLECULE TYPE: Other nucleic acid ( x i ) SEQUENCE DESCRIPTION: SEQ ID NO:31:

GTAAAACGAC GGCCAG                     16

OXIDIZED PHOSPHOLIPID DEGRADING ENZYME AND GENE THEREOF

BACKGROUND OF THE INVENTION a) Field of the Invention

This invention relates to a novel phospholipase, and more specifically to an oxidized phospholipid degrading enzyme playing an important role in the oxidized phospholipid elimination mechanism in animal cytoplasm and also to a gene coding the same.

b) Description of the Related Art

It is known that under diverse oxygen stress, a phospholipid as a membrane-forming component is oxidized to cause various troubles on an organism. The organism is considered to be equipped with a protective mechanism against such oxygen stress so that an oxidized phospholipid formed under oxygen stress would be promptly hydrolyzed by an oxidized phospholipid degrading enzyme to avoid any trouble, which could otherwise occur by a chain oxidative reaction, and also to facilitate restoration of phospholipid molecules.

Regarding the oxidized phospholipid degrading enzyme playing the important role in the protective mechanism, there is the view that phospholipase $A_2$ known to catalyze the splitting of normal phospholipids also plays the role (Sevanian, A., Stein, R. A. and Mead, J. F., Lipids 16, 781–789, 1981). For the low oxidized-phospholipid degrading activity of phospholipase $A_2$, however, it has been considered that another enzyme plays this role in actual organisms.

BRIEF DESCRIPTION OF THE INVENTION

To prevent various troubles caused by oxygen stress in an organism, it is necessary as a first step to elucidate the protective mechanism against oxygen stress in the organism and to identify an oxidized phospholipid degrading enzyme which takes part in the protective mechanism.

The present inventors started research with a view toward isolating and purifying an oxidized phospholipid degrading enzyme which exists in a tissue of an organism. First, it was however found that TLC (thin-layer chromatography), which is a conventional method for the assay of oxidized phospholipid degrading enzymes, would be able to measure only 12 samples or so at once and moreover, would take as long as 5 hours until the results are obtained and hence is not usable in view of the number of samples, deactivation of purified enzymes, etc.

An investigation was therefore conducted to devise a new method for the assay of oxidized phospholipid degrading enzymes and as a method permitting assay of 40 samples or so at once in a period as short as 2 hours or so, a method making use of $^{14}C$-labeled oxidized phosphatidylcholine (oxidized PC) as a substrate was developed.

As a result of a further investigation, it was found that an oxidized phospholipid degrading enzyme also uses 1-hexadecyl-2-acetyl-sn-glycero-3-phospho-choline (platelet activating factor, PAF) as a substrate like oxidized PC. Based on this finding, the present inventors also developed a method for the assay of an oxidized phospholipid degrading enzyme, said method making use of $^{3}H$-labeled PAF as a substrate.

The above method which makes use of PAF has advantages over the above-described system making use of oxidized PC, such as (1) since PAF is a simple substance, the system can be simplified compared with the use of oxidized PC which is a mixture, (2) because the product of hydrolysis at sn-2 is acetic acid, this hydrolyzate can be separated completely from unreacted PAF by devising solvent fractionation as needed, and (3) for the availability of $^{3}H$-labeled PAF on the market, a stable assay system can be constructed.

By the above assay method, the present inventors measured the oxidized phospholipid degrading enzyme activity in soluble fractions of various organs of animals, leading to the finding that the enzyme activity is distributed widely in organs such as brain and kidneys.

The present inventors then chose bovine brain as a source for the provision of an oxidized phospholipid degrading enzyme and by using a variety of isolation and purification methods, increased its purity while monitoring its enzyme activity by the assay method described above. As a result, an oxidized phospholipid degrading enzyme has been obtained in a substantially pure form.

Further, a gene which codes the oxidized phospholipid degrading enzyme has also been found by a known method from the peptide sequence of the enzyme.

The present invention has been completed based on these findings, and provides the oxidized phospholipid degrading enzyme—which plays an important role in the oxygen stress preventive mechanism in organisms—and also the gene coding the enzyme, said gene being important for the synthesis of the enzyme by genetic engineering.

The oxidized phospholipid degrading enzyme according to this invention selectively degrade an oxidized phospholipid, whereby it can be used as a pharmaceutical or biochemical reagent for the prevention or treatment of diseases caused by oxidation of a phospholipid in an organism, for example, tissue damages due to ischemic re-perfusion, inflammation, hepatophathy by an organic chlorine compound or the like, and adult respiratory distress syndrome.

The gene which codes the oxidized phospholipid degrading enzyme according to this invention makes it possible to obtain the enzyme of this invention in a large quantity by conducting its expression in a host such as E. coli by gene manipulation.

It is also possible to construct an assay system for the evaluation of each oxidized phospholipid elimination mechanism by introducing the above gene in CHO cells or the like.

DETAILED DESCRIPTION OF THE INVENTION

Figure 1:
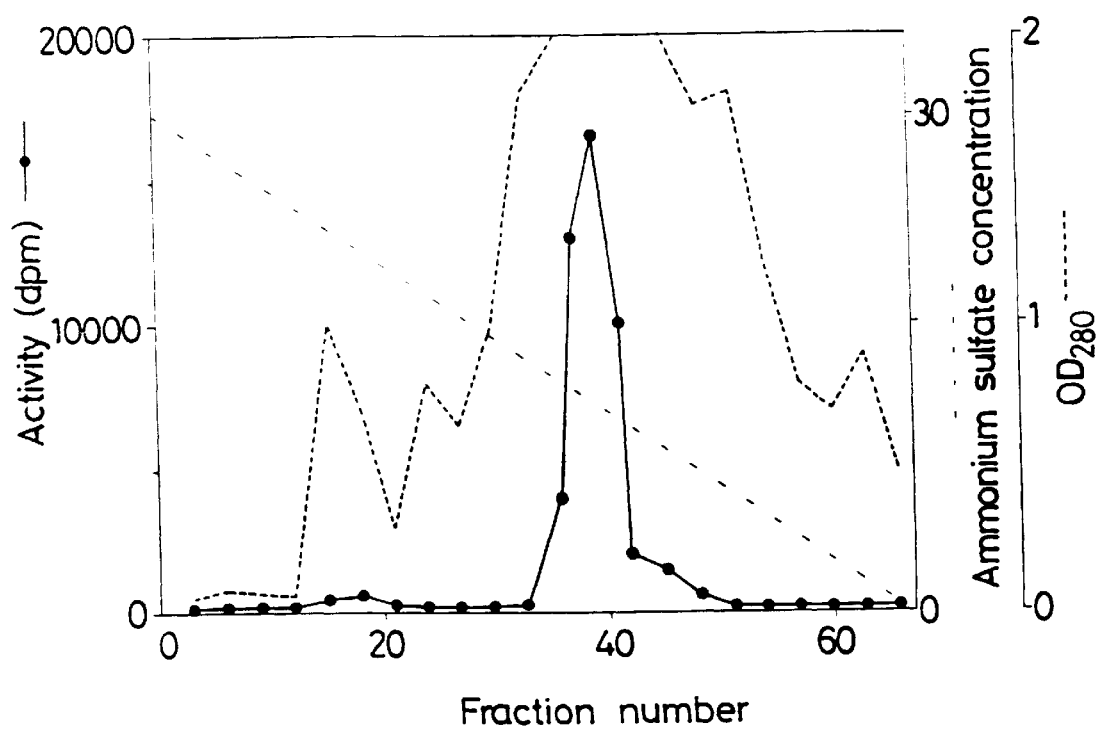
FIG. 1 is a diagram showing chromatography on a "butyl TOYOPEARL" column.

Although the oxidized phospholipid degrading enzyme according to the present invention can be obtained from various tissues of animals or the like containing the enzyme by isolating and purifying it in a manner known per se in the art while using the oxidized phospholipid degrading activity as an index, it is preferred to use bovine brain for the reasons to be described next.

In the brain, (1) the concentration of α-toco-pherol (vitamin E), an important antioxidant, is low compared with other organs (Faud, J. and McNally, W. P., Arch. Int. Parmacodyn. 250, 4–17, 1981), (2) ischemic re-perfusion often occurs, (3) the oxygen consumption per unit weight is far higher compared with other organs, and (4) for reasons such that cranial nerve cells undergo a severe damage once a trouble occurs because they are practically unregenerated through divisions, the content of an oxidized phospholipid degrading enzyme effective for the prevention of this trouble is expected to be high.

Further, to obtain an enzyme whose content is low in an organism, a great deal of raw material is needed. As a large animal which now enables easy provision of a large number of brains, bovine is most suited.

It is therefore preferred to use bovine brains as a raw material for the provision of the oxidized phospholipid degrading enzyme.

Using bovine brains as an illustrative raw material, a specific description will hereinafter be made of procedures for obtaining the oxidized phospholipid degrading enzyme.

As bovine brains to be used as a raw material for the provision of the oxidized phospholipid degrading enzyme, is used gray matter which remains after removal of surface blood vessels, white matter and diencephalon from whole bovine brains immediately after slaughter.

After these bovine brains are washed with a suitable buffer (for example, 10 mM Tris-HCl buffer containing 250 mM sucrose and 1 mM EDTA and having a pH of 7.4), they were homogenized with the same buffer and then centrifuged to obtain a soluble fraction of cytoplasm.

The soluble fraction of cytoplasm is fractionated with ammonium sulfate by a method known per se in the art, thereby obtaining a 45%–60% pellet (i.e., a precipitate fraction formed when ammonium sulfate is added to a 45% saturation supernatant until the concentration of ammonium sulfate reaches 60% saturation).

While making combined use of hydrophobic chromatography, ion exchange chromatography, adsorption chromatography, gel filtration chromatography and the like, this pellet fraction is purified until a single peak is obtained on a "Superose 12 Column" (Pharmacia AB), so that the oxidized phospholipid degrading enzyme can be obtained.

The enzyme so obtained had the following physical and chemical properties:

(1) Action:
The enzyme hydrolyzes a 1-acyl-2-ω-carboxyfatty acid acyl-3-phosphatidylcholine as a substrate at the 2-ester bond thereof to form 1-acyl-2-lyso-3-phos-phatidylcholine.

(2) Substrate specificity:
The enzyme hydrolyzes a 1,2-diacyl-3-phosphatidylcholine in which the 2-acyl group is a ω-carboxyfatty acid acyl group or an acetyl group, but does not hydrolyze a 1,2-diacyl-3-phosphatidylcholine in which the 2-acyl group is a fatty acid acyl group having at least 6 carbon atoms.

(3) Optimal reaction pH:
pH 7.0 to 8.0

(4) Inhibitors:
Enzyme reactions are inhibited by 1 mM p-bromophenacyl bromide (BPB) or 1 mM diisopropylfluorophosphate (DFP) but are not inhibited by 1 mM iodoacetamide (IAM).

(5) Activation by calcium ions:
Enzyme activity is slightly enhanced by 4 mM calcium chloride.

(6) Molecular mass:
95±5 kDa (by gel filtration).

(7) Subunits:
The enzyme is composed of three subunits whose molecular masses have been found to be 29 kDa, 30 kDa and 45 kDa, respectively, by SDS-polyacrylamide electrophoresis.

As described above under (7) and will also be described in detail in Examples, the oxidized phospho-lipid degrading enzyme has been ascertained from the results of SDS-polyacrylamide electrophoresis (SDS-PAGE) to be a heterotrimer composed of three subunits of 45 kDa, 30 kDa and 29 kDa, respectively.

By subjecting the above enzyme to treatment on a heparin Sepharose column or sulfated Cellulofine column, a 30 kDa–29 kDa complex without the 45 kDa subunit was obtained. The complex so obtained exhibited similar activity.

On the other hand, reaction of the enzyme with $^3$H-labeled diisopropylfluorophosphate results in specific labeling of the 29 kDa subunit, so that the activity of the enzyme is considered to be attributed to active serine residual groups contained in the subunit. Accordingly, the 29 kDa subunit can be used by itself as a synthesized oxidized phospholipid degrading enzyme or the like.

To determine the primary structure of each of the subunits making up the oxidized phospholipid degrading enzyme of this invention, it is only necessary to subject their corresponding full-length cDNA's to cloning to determine the base sequences of the cDNA's and then to determine amino acid sequences corresponding to the base sequences, respectively.

Described specifically, the enzyme according to this invention is degraded to obtain peptide fragments corresponding to the respective subunits and their amino acid sequences are determined. Oligomers having base sequences corresponding to the respective amino acid sequences are then synthesized. Using PCR, full-length cDNA's are cloned from a cDNA library.

The base sequences of the full-length cDNA's are determined by an automated sequencer. Subsequent to estimation of coding initiator codons, the corresponding amino acid sequences are determined so that the amino acid sequences of the respective subunits can be determined.

The thus-obtained base sequences of the genes which code the individual subunits of the above enzyme are as shown in a Sequence Listing to be described subsequently herein, namely, the 29 kDa subunit is represented by SEQ ID NO:4, the 30 kDa subunit by SEQ ID NO:6, and the 45 kDa subunit by SEQ ID NO:7, respectively.

Further, the amino acid sequences of the respective subunits of the above enzyme, said amino acid sequences being estimated from the above base sequences, are also as shown in the Sequence Listing, namely, the 29 kDa subunit is represented by SEQ ID NO:1, the 30 kDa subunit by SEQ ID NO:2, and the 45 kDa subunit by SEQ ID NO:3, respectively.

The term "an amino acid sequence having homology" as used herein means that the amino acid sequence has the same function as the peptide represented by the preceding amino acid sequence although the former sequence have at parts thereof substitution, deletion, addition and/or the like of amino acids.

The oxidized phospholipid degrading enzyme of this invention obtained as described above selectively degrades oxidized phospholipids as demonstrated in the Examples to be described subsequently herein.

The enzyme is therefore believed to degrade an oxidized phospholipid formed as a result of oxidation of plasma membranes or organelle membranes so that it protects membranes from damages, which would otherwise occur by a chain oxidative reaction, and also to promote restoration of phospholipid molecules.

The present invention will hereinafter be described in further detail by the following Examples and Reference Examples. It should however be borne in mind that the present invention is by no means limited to or by such Examples.

Reference Example 1

Preparation of Substrate for the Oxidized Phospholipid Degrading Enzyme (a) Synthesis of 1-palmitoyl-2-[1-$^{14}$C]-linoleoyl-sn-glycero-3-phosphocholine (2-$^{14}$C-linoleoyl PC)

Mixed were 5 $\mu$mol of 1-palmitoyl-sn-glycero-3-phosphocholine (lyso PC) (product of Bachem Feinchemikalien AG) and 3.5 $\mu$mol (203 $\mu$Ci) of [1-$^{14}$C]-linoleic acid [product of New England Nuclear Company]. Subsequent to evaporation, the resulting mixture was suspended in 6.25 ml of a phosphated buffer (pH 7.4).

The suspension was then added with 1.5 ml of a microsome fraction (7.2 mg/ml) of rat liver, 1.25 ml of 100 mM ATP, 1.25 ml of 100 mM $MgCl_2$ and 0.75 ml of 5 mM CoA, followed by incubation at 37° C. for 30 minutes. After total lipids were extracted by the Bligh-Dyer method (Bligh, E. G. and Dyer, W. J., Can. J. Biochem. Physiol., 37, 911, 1959), the solvent was distilled off.

The residue was dissolved in a small amount of chloroform and then applied to chromatography on a "CM Cellulose 52 Column" (1.5×5.0 cm) (product of Whatman Company). The column was washed with a chloroform-methanol (99:1) solvent system to elute unreacted linoleic acid, followed by the elution with a chloroform-methanol (96:4) solvent system. While monitoring by TLC, the whole eluate fractions were collected. Subsequent to elimination of the solvent, the residue was dissolved in a chloroform-methanol (2:1) solvent system and was then stored. The recovery rate of radioactivity was about 55%.

(b) Adjustment of Specific Radioactivity and Oxidation

The 2-$^{14}$C linoleoyl PC (hot) obtained above in step (a) and non-radioactive (cold) 2-linoleoyl PC (product of Serdary Research Laboratories Inc.) were mixed to adjust the specific radioactivity to about 3,000 dpm/nmol. Following the method proposed by Gerlach et al. (Gerlach, E. and Deuticke, B., Biochem. J., 337, 447, 1969), phosphorus was quantitatively analyzed to determine the exact specific radioactivity.

Subsequent to the adjustment of the specific radioactivity, the PC was oxidized following the procedures proposed by Shimojo et al. (Shimojo, T., Abe, M. and Ohta, M., J. Lipid Res., 15, 525–527, 1974), Described specifically, the solvent was removed from 7.5 pmol of the PC which had been adjusted in specific radioactivity, followed by the dissolution of the residue in 1.5 ml of 90% acetic acid. To the solution, an oxidizing solution which was an aqueous solution of 24 mM potassium permanganate and 20 mM of sodium periodate was added 200 $\mu$l by 200 $\mu$e 20 times (4 ml in total) under stirring. The resulting mixture was stirred at room temperature for 2 hours.

After completion of the reaction, a small amount of 20% sodium sulfite was added to deactivate any unreacted oxidizing agents. The resulting mixture was adjusted to pH 2 with 1N hydrochloric acid and then extracted three times by the Bligh-Dyer method. All the extracts were combined, from which the solvent was eliminated. The residue was dissolved in a small amount of chloroform and then applied to a thin-layer chromatography (TLC) while using preparative silica gel plates. The residue was developed by a chloroformmethanol-ammonia (65:35:10) mixture. As controls, standard samples of 2-linoleoyl PC and 2-azelaoyl PC were also developed.

After the development, plates corresponding to oxidized PC were collected with reference the positions of the controls identified by iodine staining and the distribution of radioactivity determined by a TLC scanner. Under acidic conditions of acetic acid, those plates were subjected three times to extraction by the Bligh-Dyer method. After the solvent was eliminated, the residue was dissolved in a chloroform-methanol (2:1) solvent system and then stored at −20° C.

Reference Example 2

Measurement of the Activity of the Oxidized Phospholipid Degrading Enzyme by Using Oxidized PC To measure the activity of the oxidized phospholipid degrading enzyme by using oxidized PC, Tris-HCl buffer (final concentration: 50 mM, pH 7.4) which contained as a substrate 20 nmol (6,000 dpm) of the oxidized PC obtained in Reference Example 1 was added with 5 mM EDTA or 4 mM $CaCl_2$ as needed, to which the sample (enzyme source) to be measured was added to give a total volume of 250 $\mu$l.

They were mixed in a test tube over ice and then incubated at 37° C. for 30 minutes. Thereafter, 560 $\mu$l of a chloroform-methanol (1:1) mixture were added to terminate the reaction. After the resulting mixture was vigorously mixed for 5 minutes by a vortex stirrer, the mixture was centrifuged for 5 minutes at 3,000 rpm to separate it into two layers. From the upper layer, 300 $\mu$l were collected, in which 3 ml of "Clearsol I" (product of NACALAI TESQUE INC.) were mixed. The radioactivity was measured by a liquid scintillation counter. From the intensity of the radioactivity, the amount of the dicarboxylic acid formed as a result of 2-hydrolysis was calculated to determine the enzyme activity.

Reference Example 3

Measurement of the Activity of the Oxidized Phospholipid Degrading Enzyme by Using PAF (a) Preparation of substrate 1-Hexadecyl-2-[$^3$H]acetyl-sn-glycero-3-phospho-choline (hot PAF, product of Bachem Feinchemikalien AG) and non-radioactive PAF (cold PAF) were mixed to adjust the specific radioactivity to about 3,000 dpm/nmol. Phosphorus was quantitatively analyzed likewise to measure the exact specific radioactivity.

(b) Measurement of the activity of the oxidized phospholipid degrading enzyme by using PAF Measurement of the oxidized phospholipid degrading enzyme by using PAF was conducted in a similar manner to Reference Example 2. Namely, Tris-HCl buffer (final concentration: 50 mM, pH 7.4) which contained as a substrate 20 nmol (6,000 dpm) of the labeled PAF obtained in step (a) was added with 5 mM EDTA or 4 mM $CaCl_2$ as needed, to which the sample (enzyme source) to be measured was added to give a total volume of 250 $\mu$l.

They were mixed in a test tube over ice and then incubated at 37° C. for 30 minutes. Thereafter, 2.5 ml of a chloroform-methanol (4:1) mixture were added to terminate the reaction. Subsequent to addition of 0.25 ml of water, the resulting mixture was vigorously mixed for 5 minutes by a vortex stirrer and then centrifuged for 5 minutes at 3,000 rpm to separate it into two layers. From the upper layer, 600 $\mu$l were collected, in which 3 ml of "Clearsol I" (product of NACALAI TESQUE INC.) were mixed. The radioactivity was measured by a liquid scintillation counter. From the intensity of the radioactivity, the amount of acetic acid formed as a result of 2-hydrolysis was calculated to determine the enzyme activity.

Example 1

Purification of the oxidized phospholipid degrading enzyme from bovine brain (a) Preparation of soluble fraction of cytoplasm of bovine brain Surface blood vessels, white matter and diencephalon were removed from about 500 g of bovine brain, whereby about 300 g of gray matter were obtained. After it was washed three times with 10 mM Tris-HCl buffer containing 250 mM sucrose and 1 mM EDTA (pH 7.4, hereinafter called the "SET buffer"), about 600 ml of the SET buffer were added, followed by homogenization for 30 seconds in a "National Mixer, Model:MX-V350".

The above procedures were repeated 5 times in total. The resulting homogenate was centrifuged for 20 minutes in a TOMMY centrifugal machine (No. 9, 10 krpm) to remove solid matter. The supernatant so formed was subjected to 100,000 g's ultracentrifugation ("Hitachi-70P, RP42" rotor, 40 krpm) so that about 570 ml of a soluble fraction of cytoplasm of bovine brain was obtained. The protein concentration measured by the Lowry method was about 11.6 mg/ml.

(b) Fractionation with ammonium sulfate

To 300 ml of the soluble fraction of the cytoplasm of the bovine brain obtained above in step (a), solid ammonium sulfate (enzyme purification grade, product of WAKO PURE CHEMICAL INDUSTRIES, LTD.) was added little by little in ice water under stirring by a method known per se in the art so that the concentration of ammonium sulfate reached 45% saturation in terms of the Osborne's saturation degree. After the completion of the addition, the resulting mixture was stirred for further 30 minutes. The mixture so obtained was then centrifuged for 20 minutes in the TOMMY centrifugal machine (No. 9, 10 krpm) to separate it into a precipitate and a supernatant. Solid ammonium sulfate was added further to the supernatant to give 60% saturation. The resulting mixture was treated similarly to obtain a precipitate (this fraction will be called "45–60% pellet").

(c) "Butyl TOYOPEARL" column chromatography

The 45–60% pellet obtained above in step (b) was suspended in 150 ml of 10 mM Tris-HCl buffer which contained 1 mM EDTA. The suspension was then dialyzed against 5,000 ml of the same buffer. After the dialysis, ammonium sulfate was added to 30% saturation and a precipitate formed in a small amount was removed by centrifugation (3,500 rpm, 10 minutes). The supernatant of the centrifugation was applied to a 2.5×18 cm column packed with "Butyl TOYO-PEARL 650 M" (product of TOSOH CORPORATION) which had been equilibrated with the above buffer containing ammonium sulfate at 30% saturation. The column was washed with the above buffer containing 30% saturation of ammonium sulfate, followed by elution with a 500 ml linear gradient of ammonium sulfate (from 30% saturation to 0% saturation) in the above buffer.

While monitoring by 280 nm ultraviolet absorption, the eluate was fractionated 8 ml by 8 ml. The activity of each fraction was measured with a PAF system which contained 5 mM EDTA. A main active fraction was observed in registration with an ultraviolet absorption peak of a fraction eluted around 10% saturation ammonium sulfate concentration.

The results are shown in FIG. 1.

(d) "DEAE Sepharose CL-6B" column chromatography

The active fraction obtained above in step (c) was dialyzed against 5,000 ml of 10 mM Tris-HCl buffer (pH 7.4, hereafter called TEG buffer) which contained 1 mM EDTA and 10% glycerol. After the dialysis, the dialyzed solution was applied to a column (1.5×15 cm) packed with "DEAE Sepharose CL-6B" (product of Pharmacia AB) which had been equilibrated with TEG buffer. The column was washed with TEG buffer, followed by elution with a 400 ml linear gradient of NaCl (0 mM to 300 mM) in TEG buffer.

While monitoring by 280 nm ultraviolet absorption, the eluate was fractionated 6 ml by 6 ml. The activity of each fraction was measured with a PAF system which contained 5 mM EDTA. A main active fraction was observed around 130 mM NaCl concentration separately from an ultraviolet absorption peak.

Figure 2:
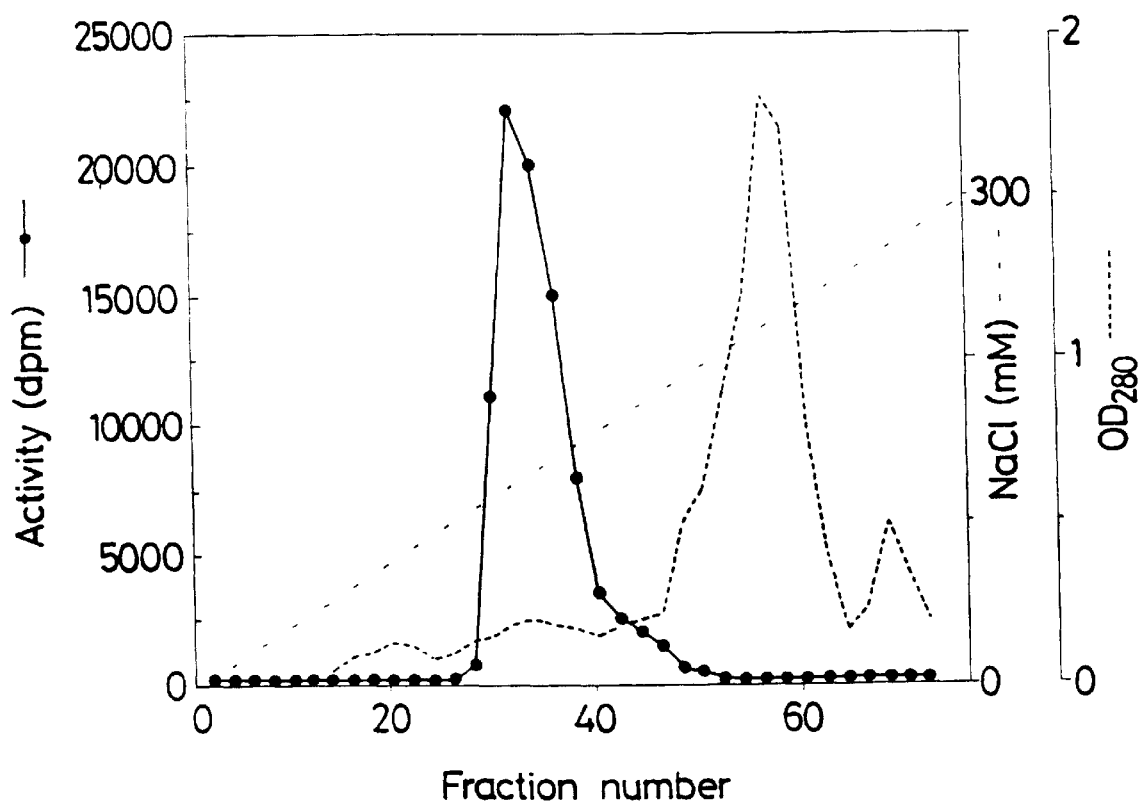
FIG. 2 is a diagram showing chromatography on a "DEAE (diethylaminoethyl ethyl) Sepharose CL-6B" column.

The results are shown in FIG. 2.

(e) Hydroxyapatite column chromatography

The active fraction obtained above in step (d) was applied, as was, to a hydroxyapatite column (1.5×15 cm) which had been equilibrated with potassium-phosphated buffer (pH 6.8, hereinafter called "buffer A") which contained 5 mM 2-mercaptoethanol and 10% glycerin. The column was washed with buffer A, followed by elution with a 400 ml linear gradient of $KH_2PO_4$—KOH (10 mM to 300 mM).

While monitoring by 280 nm ultraviolet absorption, the eluate was fractionated 6 ml by 6 ml. The activity of each fraction was measured with a PAF system which contained 5 mM EDTA. A main active fraction was observed around a $KH_2PO_4$—KOH concentration of 110 mM in registration with an ultraviolet absorption peak. The purity of the enzyme in this purification step was about 70%.

Figure 3:
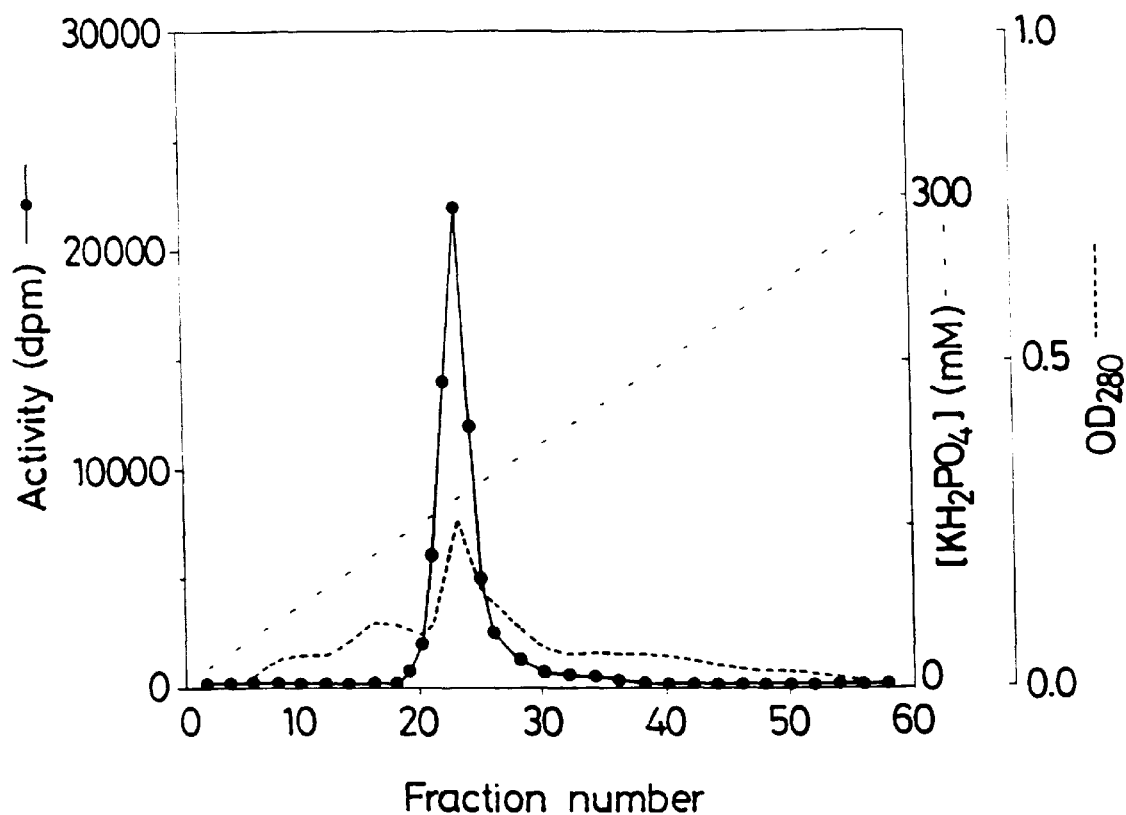
FIG. 3 is a diagram showing chromatography on a "hydroxyapatite" column.

The results are shown in FIG. 3.

(f) "Mono Q FPLC" column chromatography

The active fraction obtained above in step (e) was dialyzed against 3,000 ml of buffer A. Using an "FPLC system" (product of Pharmacia AB), the dialyzed solution was caused to adsorb at a flow rate of 0.5 ml/min on a "mono Q column" which had been equilibrated with buffer A. The column was washed at the same flow rate with 10 ml of buffer A, followed by elution with a 28 ml linear gradient of NaCl (0 mM to 200 mM) in buffer A.

While monitoring by 280 nm ultraviolet absorption, the eluate was fractionated 0.5 ml by 0.5 ml. The activity of each fraction was measured with a PAF system which contained 5 mM EDTA. A main active fraction was observed around an NaCl concentration of 125 mM in registration with an ultraviolet absorption peak.

Figure 4:
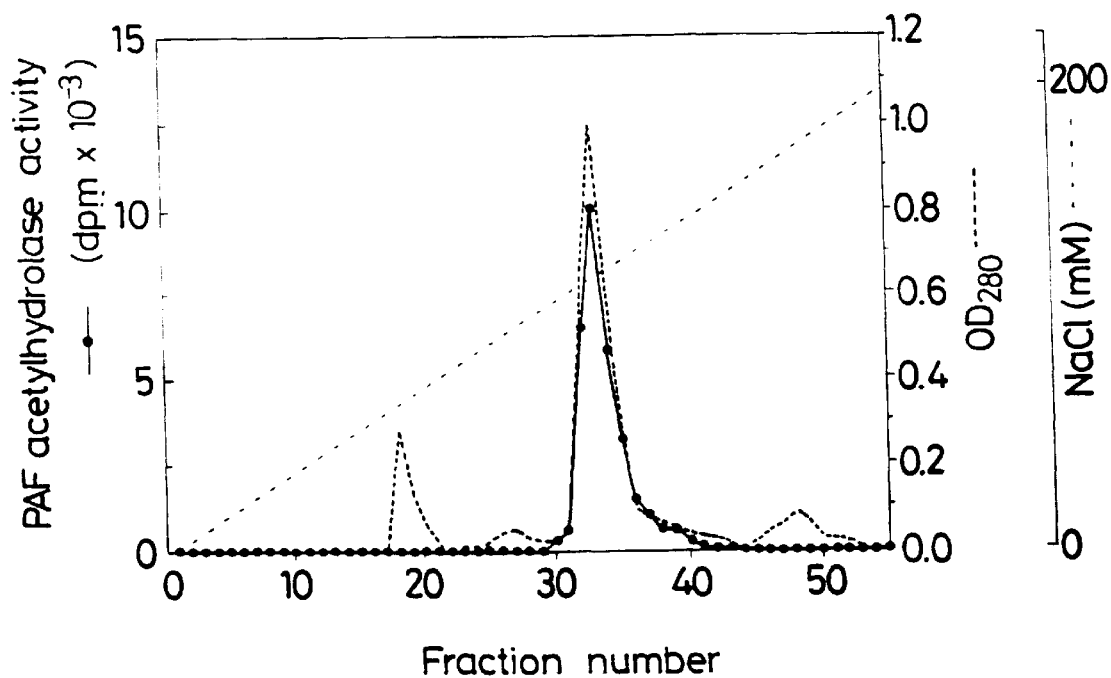
FIG. 4 is a diagram showing chromatography on a "mono Q FPLC, fast protein liquid chromatography" column.

The results are shown in FIG. 4.

(g) Verification of the purity by gel filtration of the purified sample

Figure 5:
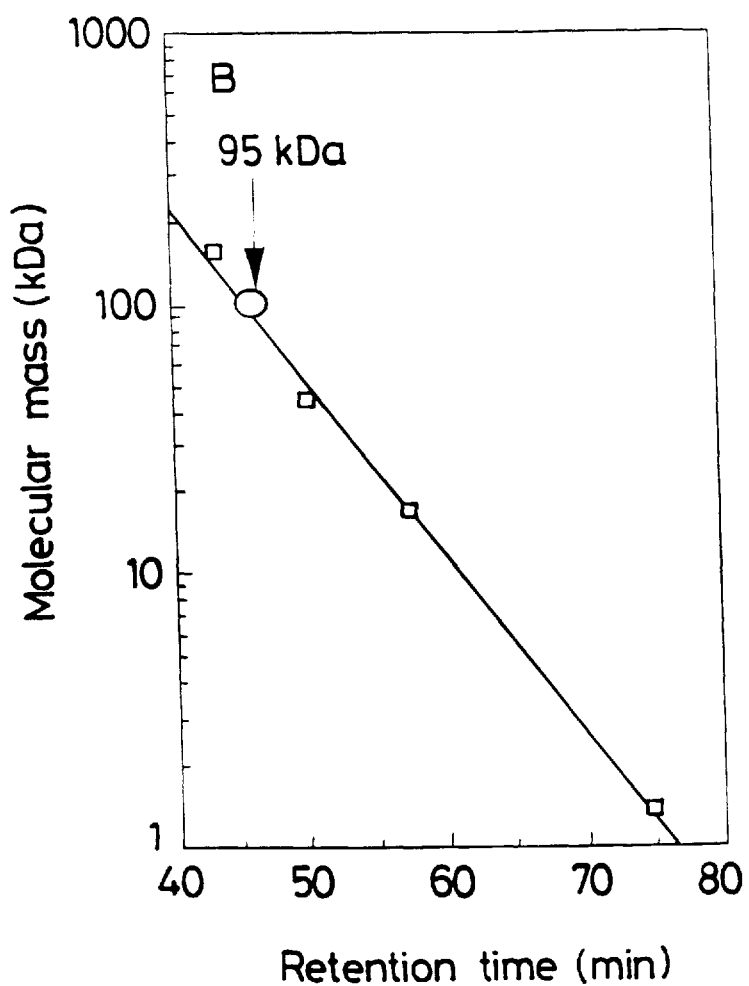
FIG. 5 is a diagram showing the results of gel filtration.

Using the FPLC system, 100 $\mu$t of the active fraction obtained above in step (f) were applied at a flow rate of 0.25 ml/min on a "Superose 12 Column" (product of Pharmacia AB) which had been equilibrated with buffer A. When the column was developed at the same flow rate while monitoring by 280 nm ultraviolet absorption, a single-peak absorption was observed at 95 kDa as illustrated in FIG. 5. Enzyme activity was also observed in registration with that peak.

Purification data obtained in various purification steps described so far are presented in Table 1.

TABLE 1

| Purification step | Total* activity | Total proteins (mg) | Specific** activity | Purification degree (times) | Recovery rate (%) |
|---|---|---|---|---|---|
| Soluble fraction | 4800 | 6600 | 0.72 | 1 | 100 |
| Ammonium sulfate fractionation | 3360 | 690 | 4.9 | 68 | 70.0 |
| Butyl TOYOPEARL | 1520 | 81 | 18.8 | 26.3 | 31.7 |
| DEAE Sepharose | 1210 | 2.7 | 448 | 622 | 25.2 |
| Hydroxy-apatite | 907 | 0.9 | 1008 | 1400 | 18.9 |
| Mono Q FPLC | 435 | 0.3 | 1450 | 2010 | 9.1 |

*unit: nmol/min.
**unit: nmol/min/mg.

Example 2

Figure 6:
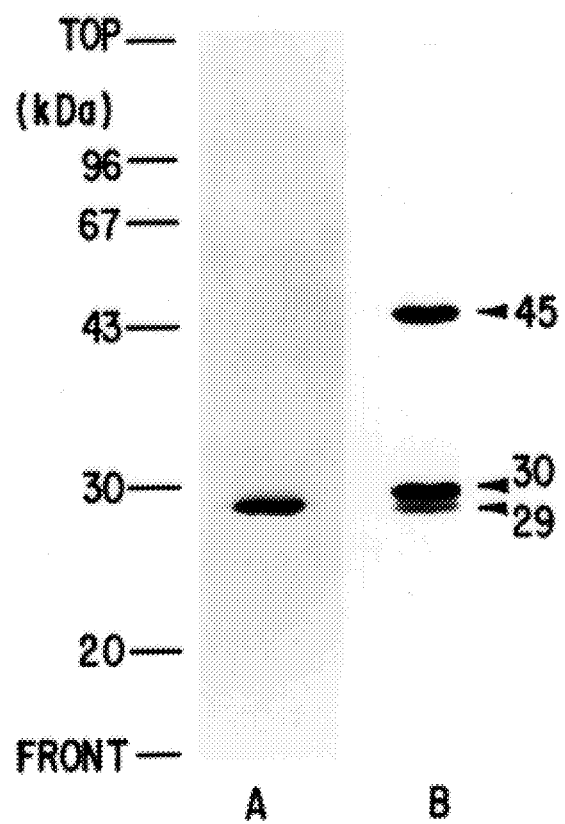
FIG. 6 is a photograph showing the results of measurement of molecular mass by SDS-PAGE.

Properties of the Oxidized Phospholipid Degrading Enzyme and Analysis of Its Structure (a) Measurement of molecular mass In step (g) of Example 1, the molecular mass of the present enzyme was determined to be about 100 kDa. When the present enzyme was subjected to an SDS-PAGE analysis at a gel concentration of 12% in the presence of 2-mercaptoethanol in accordance with the method proposed by Laemmli (Laemmli, U.K., Nature, 227, 680–685, 1970), three spots corresponding to 29 kDa, 30 kDa and 45 kDa were obtained as shown in FIG. 6.

It was suggested from the foregoing that the present enzyme has a heterotrimer structure consisting of three subunits of 29 kDa, 30 kDa and 45 kDa.

(b) Isolation of the 45 kDa subunit by heparin Sepharose

Against buffer A, 15 ml of the roughly purified fraction obtained in step (e) of Example 1 were dialyzed. The solution so dialyzed was then applied to a column (1×5 cm) of "heparin Sepharose" (product of Pharmacia AB) which had been equilibrated with buffer A, whereby about 80% of the enzyme activity passed through the column without adsorption. When the column was washed with buffer A subsequent to the passage of the dialyzed solution, the activity was gradually eluted with tailing.

After the column was washed with about 30 ml of buffer A, the enzyme was eluted with a 30 ml linear gradient of NaCl (0M to 1.5M) in buffer A. The enzyme activity was eluted around about 0.3M NaCl concentration. Those fractions were subjected to an SDS-PAGE analysis by the method of step (a), whereby three spots were observed at 20 kDa, 30 kDa and 45 kDa with respect to the flow-through fractions and two spots were observed at 29 kDa and 30 kDa with respect to the eluate fractions. Further, the fractions eluted around about 0.6M NaCl concentration gave only one spot at 45 kDa.

The eluate fraction obtained in step (b) gave a single peak at a molecular mass of about 50 kDa when analyzed in accordance with the method in step (g) of Example 1. From this, the above fraction was estimated to have a structure similar to the original enzyme except for the deletion of the 45 kDa subunit. Further, that eluate fraction had similar activity to the original enzyme.

(c) Measurement of the substrate specificity of the purified enzyme

The substrate specificity of the purified enzyme obtained in step (f) of Example 1 was investigated in relation to PAF, PC, phosphatidylethanolamine (PE), lyso PC and oxidized PC. Its degrading activity against PC, PE and lyso PC was measured in the presence of 4 mM $CaCl_2$ in accordance with the method proposed by Dole et al. (Dole, V.P. and Menertz, H., J. Biol. Chem., 253, 2595 (1960)). The activity against oxidized PC and PAF was measured following the method in Reference Examples 2 and 3. The results are presented in Table 2.

TABLE 2

| Substrate Specificity | |
|---|---|
| Substrate | Specific activity (nmol/min/mg) |
| PAF | 1.45 |
| PC | Not degraded |
| PE | Not degraded |
| Lyso PC | Not degraded |
| Oxidized PC | 0.86 |

From the results in Table 2, it has been found that the present enzyme shows degrading activity against oxidized PC and PAF, does not show any degrading activity against normal PC and PE and further shows absolutely no degrading activity against lyso PC already hydrolyzed at the 2-site. Namely, the present enzyme was estimated to act in the first step of degradation of an oxidized phospholipid.

(d) Measurement of the sensitivity of the purified enzyme to inhibitors

Portions of the purified enzyme (40 mg/ml) obtained in step (f) of Example 1 were added iodoacetamide (IAM), p-bromophenacyl bromide (BPB) and 10 diisopropyl fluorophosphate (DFP), respectively, to give final concentrations 0.1 mM and 1 mM. After the resulting mixtures were preincubated at room temperature for 10 minutes, changes in the activity were investigated. The results are presented in Table 3.

TABLE 3

| Sensitivity to Enzyme Inhibitors | | |
|---|---|---|
| Enzyme inhibitor | Final concentration (mM) | Inhibition (%) |
| IAM | 0.1 | 0 |
|  | 1.0 | 0 |
| BPB | 0.1 | 20 |
|  | 1.0 | 97 |
| DFP | 0.1 | 96 |
|  | 1.0 | 99 |

As is shown in Table 3, the purified enzyme was strongly inhibited by DFP and was also inhibited by BPB as the concentration as high as 1 mM, but was not inhibited at all by IAM. From this, it was estimated that serine residual groups and histidine residual groups are contained as essential groups in the active center of the present enzyme.

(e) Identification of an activity-bearing subunit by [$^3$H]-labeling

Since the present purified enzyme is strongly inhibited by DFP as shown above in step (d), an activity bearing subunit was identified using labeled DFP. Described specifically, [$^3$H]-labeled DFP (10 μCi, 1.16 nmol, product of New England Nuclear Company) was added to 50 μg of the purified enzyme (50 μl of a solution in buffer A). After the resulting mixture was incubated at room temperature for 30 minutes, an SDS-PAGE analysis was conducted following the method in step (a) of Example 2. Subsequence to CBB staining, the resulting mixture was treated for 1 hour with an enhancer ("En³Hance, product of New England Nuclear Company).

After the treatment, the gel was dried and in a form closely contacted with a film ("XRP-5", Eastman Kodak Company), was exposed to light at −70° C. for 4 days. As a result, only the 29 kDa subunit was specifically labeled. It was hence revealed that active serine residual groups were contained therein.

(f) Measurement of the pH dependency of the enzyme activity

Using the method in Reference Example 3, the enzyme activity was measured in the presence of 5 mM EDTA while varying the reaction pH 0.5 by 0.5 in a range of from 4.0 to 9.0 by changing the buffer (employed were 100 mM acetate buffer from pH 4.0 to pH 5.5, 100 mM Tris-maleate buffer from pH 5.5 to pH 7.0, and 100 mM Tris-HCl buffer from pH 7.0 to pH 9.0). As a result, the optimal pH for the present enzyme was found to range from 7.0 to 8.0

(g) Evaluation of influence of calcium ions on the enzyme activity

The enzyme activity was measured by the measuring method of Reference Example 3 except that 4 mM CaCl$_2$ was added instead of 5 mM of EDTA. As a result, it has been found that the enzyme activity is enhanced by about 1.3 times by the addition of calcium.

Example 3

Determination of the primary structures of peptide fragments of the purified enzyme To analyze the primary structure of the present enzyme so purified, the enzyme was converted to a reduced pyridyl ethyl form and then split with API and the determination of the structures of individual peptide fragments was attempted. After the API splitting, the individual peptide fragments were recovered by reverse phase HPLC. With respect to ten peptide fragments, their structures were determined by an amino acid sequencer in accordance with a method commonly employed in the art. The amino acid sequences of the respective peptide fragments will hereinafter be indicated by SEQ. ID Nos. 10–19, respectively.

(SEQ. ID. No:10)

Ile Val Val Val Trp Val Gly Thr Asn Asn His
1           5                    10

Gly His Thr Ala Glu
            15

(SEQ. ID. No:11)

Ala Ile Val Gln Leu Val Asn Glu Arg Gln Pro Gln Ala
1             5                 10

Arg Val Val Val Leu Gly Leu Leu Pro Arg Gly Gln His Pro
    15                  20                  25

(SEQ. ID. No:12)

Asp Lys Glu Pro Glu Val Val Phe Ile Gly Asp Ser Leu
1             5                 10

Val Gln Leu Met His Gln Cys Glu Ile Trp Arg Glu Leu
    15                  20                  25

Phe Ser Pro Leu His Ala Leu Asn Phe Gly Ile
            30                  35

(SEQ. ID. No:13)

Asp Lys Glu Pro Asp Val Leu Phe Val Gly Asp Ser Met
1             5                 10

Val Gln Leu
    15

(SEQ. ID. No:14)

Ile Ile Val Leu Gly Leu Leu Pro Arg Gly Glu Lys Pro
1             5                 10

Asn Pro Leu Arg Lys
    15          18

(SEQ. ID. No:15)

Leu Ala Asn Val Gln Leu Leu Asp Thr Xaa Gly Gly Phe
1             5                 10

Val His Ser Asp Gly Ala Ile Ser Cys His Asp Met Phe
    15                  20                  25

Asp Phe Leu His
            30

(SEQ. ID. No:16)

Val Leu Ser Gln Arg Gln Arg Asp Glu Leu Asn Arg Ala
1             5                 10

Ile Ala Asp Tyr Leu Arg Ser Asn Gly Tyr Glu Glu Ala
    15                  20                  25

Tyr (SEQ. ID. No:17)

Thr Phe Thr Gly His Arg Glu Trp Val Arg Met Val Arg
1             5                 10

Pro Asn Gln Asp Gly Thr
    15              19

(SEQ. ID. No:18)

Thr Leu Asn Ala His Glu His Phe Val Thr Ser Leu Asp
1             5                 10

Phe His Lys
    15

(SEQ. ID. No:19)

Val Trp Glu Cys Arg
1             5

Example 4

Determination of the structures of the respective subunits cDNA's of the oxidized phospholipid degrading enzyme (a) Preparation of mRNA derived from bovine brain Using "ISOGEN" (product of WAKO PURE CHEMICAL INDUSTRIES, LTD.), RNA was prepared from bovine brain. mRNA was purified using "Oligotex-dT30<Super>" (product of Takara Shuzo Co., Ltd.

(b) Preparation of a CDNA plasmid library derived from bovine brain (1) Synthesis of first strand CDNA Using "SuperScript Plasmid System" of GIBCO Company, cDNA was synthesized from 5 μg of mRNA derived from bovine brain. First, 2 μl of an NotI dT$_{17}$ primer adapter were treated with diethyl pyrocarbonate (DEPC), added to a solution of 5 µg of mRNA in 5 µl of distilled water, heated at 70° C. for 10 minutes and then cooled on ice.

Added were 4 µl of 5× first strand buffer, 2 µl of a 0.1M DTT solution, 1 µl of 10 mM dNTPs and 1 µl of DEPC-treated distilled water, followed by incubation at 37° C. for 2 minutes. "SuperScript" reverse transcriptase (5 µl) was added and subsequent to incubation for 1 hour at 37° C., the resultant mixture was placed on ice to terminate the reaction.

(2) Synthesis of second strand cDNA

To 18 µl out of the 20 µl reaction mixture employed for the synthesis of the first strand cDNA, were added 93 µl of DEPC-treated distilled water, 30 µl of 5× second strand buffer, 3 µl of 10 mM dNTPs, 1 µl of 10 U/ml *E. coil* DNA ligase, 4 µl of 10 U/ml *E. coil* DNA polymerase and 1 µl of 2 U/ml *E. coli* RNaseH. The resultant mixture was incubated at 16° C. for 2 hours, to which 2 µl (10 U) of T$_4$DNA polymerase were added, followed by incubation at 16° C. for 5 minutes.

The reaction mixture was placed on ice, to which were added 10 µl of 0.5M EDTA and 150 µl of a 25:24:1 solvent of phenol, chloroform and isoamyl alcohol. Subsequent to vigorous stirring, the mixture was centrifuged at 14,000 g's for 10 minutes and 140 µl of the supernatant were transferred to a fresh centrifuge tube. The supernatant was added with 70 µl of 7.5M ammonium acetate and 0.5 ml of ethanol, stirred and then left over at −80° C. for 30 minutes. The mixture so obtained was centrifuged at 14,000 g's for 10 minutes and subsequent to removal of the supernatant, the precipitate was washed with 0.5 ml of 70% ethanol and then dried under reduced pressure.

(3) Addition of BstXI adapter

The above cDNA precipitate was dissolved in 25 µl of DEPC-treated distilled water, followed by the addition of 10 µl of 5×T$_4$DNA ligase buffer, 10 µl of BstXI adapter (product of Invitrogen Company) and 5 µl of T$_4$DNA ligase. The resulting mixture was incubated at 16° C. for 16 hours. The mixture was then added with 50 µl of a phenol-chloroform-isoamyl alcohol (25:24:1) solvent system, followed by vigorous agitation. The mixture so obtained was centrifuged at 14,000 g's for 5 minutes, and 45 µl of the supernatant were transferred to a fresh centrifuge tube.

The supernatant was added with 25 µl of 7.5M ammonium acetate and 150 µl of ethanol. The resulting mixture was stirred and then left over at −80° C. for 30 minutes. The mixture was centrifuged at 14,000 g's for 10 minutes and the supernatant was decanted. The precipitate was washed with 0.5 ml of 70% ethanol and then dried under reduced pressure.

(4) Splitting by NotI

The above cDNA precipitate was dissolved in 41 µl of DEPC-treated distilled water, to which 5 µl of REACT 7 buffer and 4 µl of NotI were added. The resultant mixture was incubated at 37° C. for 2 hours, followed by the addition of 50 µl of a phenol-chloroform-isoamyl alcohol (25:24:1) solvent system and further by vigorous stirring. The mixture so prepared was centrifuged at 14,000 g's for 10 minutes, and 45 µl of the supernatant were transferred in a fresh centrifuge tube.

(5) Removal of the adapter and size-dependent fractionation of CDNA

The above cDNA solution was fractionated using "Quick Spin Column Linker 5" (manufactured by BMY Company), so that 50 µl of 40 ng/µl CDNA were obtained.

(6) Insertion of cDNA into plasmid vector and electroporation of *E. coll*

Added to 3 µl of the above cDNA solution was 1 µl of 29 ng/µl pRC/CMV vector (product of Invitrogen Company) which had been split with NotI and BstXI. Subsequent to the addition of 32 µl of Solution A and 4 µl of Solution B of the "Takara Ligation Kit", the resultant mixture was incubated at 16° C. for 30 minutes. The mixture was added with 40 µl of a phenol-chloroform-isoamyl alcohol (25:24:1) solvent system, vigorously stirred and then centrifuged at 14,000 g's for 10 minutes, and 35 µl of the supernatant were transferred to a fresh centrifuge tube.

The solution was added with 25 µl of 7.5M ammonium acetate and 150 µl of ethanol. The resulting mixture was stirred, left over at −80° C. for 30 minutes and then centrifuged at 14,000 g's for 10 minutes. After the supernatant was decanted, the precipitate was washed with 0.5 ml of 70% ethanol, dried under reduced pressure and then dissolved in 5 µl of distilled water. Transformation was conducted using 50 µl of "Electro Max DH10B Competent Cell" (product by BRL Company) 206,000 clones of a recombinant were obtained. Further, using 29 mg/ml pRC/CMV vector (product of Invitrogen Company) which had been split with BstXI, 505,400 clones of a recombinant were obtained likewise.

(c) Cloning of the cDNA of the 29 kDa subunit of the oxidized phospholipid degrading enzyme by MOPAC (Mixed Oligonucleotide Primed Amplification of cDNA)

Using, as a DNA template for a PCR reaction, 5 ng of the cDNA obtained above in step (b)(5), the cDNA was added with 5 µl of 10× PCR buffer, 8 µl of 1.25 mM dNTPs and 1 µl portions of 10 OD/ml primers (SEQ. ID Nos. 20 and 21 to be described below). The total volume was brought to 49 µl with DPC-treated distilled water. After the mixture so obtained was heated at 95° C. for 5 minutes, 0.25 µl of 5 U/ml TaqDNA polymerase (product of Perkin ElmerCetus Company) was added. A reaction cycle consisting of 1 minute at 94° C., 2 minutes at 58° C. and 2 minutes at 72° C. was repeated 35 times, followed by incubation at 72° C. for 10 minutes.

(SEQ. ID. No: 20)
    GGYTG NCKYT CRTTN AC
(SEQ. ID. No: 21)
    CAYCA RTGYG ARATH TG

A band of a PCR reaction product (230 bp) was observed by 2% agarose gel electrophoresis. After mineral oil was eliminated with chloroform, excess primers and dNTP were removed using "Suprec TM02" (product of Takara Shuzo Co., Ltd.). A phenol-chloroform-isoamyl alcohol (25:24:1) solvent system was then added, followed by vigorous stirring. The resulting mixture was centrifuged at 14,000 g's for 10 minutes and 45 µl of the supernatant were transferred to a fresh centrifuge tube. The supernatant was added with 25 µl of 7.5M ammonium acetate and 150 µl of ethanol, stirred and then left over at −80° C. for 30 minutes. The mixture so obtained was centrifuged at 14,000 g's for 10 minutes. After the supernatant was decanted, the precipitate was washed with 0.5 ml of 70% ethanol, dried under reduced pressure and then dissolved in 5 µl of distilled water.

Subsequent to insertion into PCRII (product of Invitrogen Company), *E. coli* DH5α Max Efficiency component cells (product of BRL Company) were subjected to transformation. With respect to the plasmid DNA as the transformant, cloning was confirmed by PCR in which M13 reverse CAGGAAACAGCTATGAC (SEQ ID NO:30) and M13(−20) forward GTAAAAC-GACGGCCAG (SEQ ID NO:31) were used. After the cloning, culture was conducted. The plasmid DNA was purified using CsCl and ultracentrifugation. The primary structural sequence of the inserted DNA fragment was determined using M13 forward primer and M13 reverse primer (by an automated sequencer manufactured by Applied Biosystems, Inc., Model 370A).

As a result, the sequence of 231 bp corresponding to Nos. 231–461 of nucleotide of SEQ. ID. No: 4 in the Sequence Listing was clarified. It contained the 24th–37th amino acid (RELFSPLHALNFGI) of SEQ. ID. No: 12, the 1st–12th amino acid (IVVVWVGTNNHG) of SEQ. ID. No: 10 and the 1st–5th amino acid (AIVQL) of SEQ. ID: No. 11, all of which were identified in Example 3. It has hence been found that the PCR reaction product is a part of the cDNA of 29 kDa subunit of the oxidized phospholipid degrading enzyme.

From the two types of oligomers (below-described SEQ. ID. Nos: 22 and 23) synthesized based on the above-found base sequence of the cDNA of the 29 kDa subunit, a full-length cDNA was cloned using PCR in accordance with the method reported by Kwiatkowski, Jr., T. J., Zoghbi, H. Y., Ledbetter, S. A., Ellison, K. A. and Chinault, A. C. in Nucleic Acids Res., 18, 7191–7192, 1990.
(SEQ. ID. No: 22)
    ATGTG CTGTG GCGTC TGG
(SEQ. ID. No: 23)
    AGTGT GCCCG TGGTT GTT The CDNA plasmid library derived from bovine brain, said library having been prepared in step (b)(6), was placed on a 96-well plate by diluting it to distribute 50 clones per well. Stationary culture was then conducted overnight. Culture fluid were recovered by combining together, as a single pool, the fluid portions from the wells in each of 12 columns.

Using 0.5 µl of the culture fluid as a DNA template for a PCR reaction, it was added with 5 µl of 10× PCR buffer, 8 µl of 1.25 mM dNTPs and 1 µl portions of the 10 OD/ml primers (SEQ. ID Nos. 23 and 24 described above). The total volume was brought to 49 µl with DPC-treated distilled water. After the mixture so obtained was heated at 95° C. for 5 minutes, 0.25 µl of 5 U/ml TaqDNA polymerase (product of Perkin Elmer Cetus Company) was added. A reaction cycle consisting of 1 minute at 94° C., 1 minute at 58° C. and 2 minutes at 72° C. was repeated 35 times, followed by incubation at 72° C. for 10 minutes. An analysis was then conducted by 2% agarose gel electrophoresis.

With respect to each pool on which a band of a PCR reaction product (107 bp) was observed by electrophoresis, a PCR reaction was conducted further. Each pool on which a band of the PCR reaction product (107 bp) was observed was lawned on the LB agar medium and each colony was subjected to a PCR reaction to achieve cloning. After the cloning, culture was conducted, and the plasmid DNA was purified using CsCl and ultra-centrifugation. The primary structural sequence of the inserted DNA fragment was then determined (by the automated sequencer manufactured by Applied Biosystems, Inc., Model 370A).

The results are presented under SEQ. ID. No: 4 in the Sequence Listing. The coding initiator methionine was considered to be the 77th nucleotide, and the 5'-untranslated region had 76 bp. The primary structural sequence of the cDNA of the 29 kDa subunit was determined. The number of amino acid residual groups in the structural gene was 232 and its estimated molecular mass was 26901.94 (including the coding initiator methionine). SEQ. ID. No: 12 was found at the amino acid numbers 36 to 72 in SEQ. ID. No: 4 in the Sequence Listing, SEQ. ID. No: 10 was found at the amino acid numbers 96 to 111 in SEQ. ID. No: 4 in the Sequence Listing, and SEQ. ID. No: 11 was found at the amino acid numbers 119 to 145 in SEQ. ID. No: 4 in the Sequence Listing.

(d) Cloning of the CDNA of the 30 kDa subunit of the oxidized phospholipid degrading enzyme by MOPAC Using as a DNA template for a PCR reaction 5 ng of the CDNA obtained in step (b)(5), the cDNA was added with 5 µl of 10× PCR buffer, 8 µl of 1.25 mM dNTPs and 1 µl portions of 10 OD/ml primers (SEQ. ID. Nos: 24 and 25 to be described below). The total volume was then brought to 49 µl with DPC-treated distilled water.
(SEQ. ID. No: 24)
    AARGA RCCCN GAYGT NYT
(SEQ. ID. No: 25)
    NARNG GRTTN GGYTT KT After the above solution was heated at 95° C. for 5 minutes, 0.25 µl of 5 U/ml TaqDNA polymerase (product of Perkin ElmerCetus Company) was added. A reaction cycle consisting of 1 minute at 94° C., 1 minute at 58° C. and 2 minutes at 72° C. was conducted 35 times, followed by incubation at 72° C. for 10 minutes. An analysis was then conducted by 2% agarose gel electrophoresis.

A band of a PCR reaction product (360 bp) was observed by electrophoresis. After mineral oil was eliminated with chloroform, excess primers and dNTPs were removed using "Suprec TM02" (product of Takara Shuzo Co., Ltd.). A phenol-chloroform-isoamyl alcohol (25:24:1) solvent system was added, followed by vigorous stirring. The resulting mixture was centrifuged at 14,000 g's for 10 minutes and 45 µl of the supernatant were transferred to a fresh centrifuge tube. The supernatant was added with 25 µl of 7.5M ammonium acetate and 150 µl of ethanol, stirred and then left over at −80° C. for 30 minutes.

The mixture so obtained was centrifuged at 14,000 g's for 10 minutes. After the supernatant was decanted, the precipitate was washed with 0.5 ml of 70% ethanol, dried under reduced pressure and then dissolved in 5 µl of distilled water. Subsequent to insertion into pCRII (product of Invitrogen Company), E. coli DH5α Max Efficiency competent cells (product of BRL Company) were subjected to transformation. With respect to the plasmid DNA as the transformant, cloning was confirmed by PCR in which M13 reverse CAGGAAACAGC-TATGAC (SEQ ID NO:30) and M13(−20) forward GTAAAACGACGGCCAG (SEQ ID NO:31) were used. After the cloning, culture was conducted. The plasmid DNA was purified using CsCl and ultracentrifugation. The primary structural sequence of the inserted DNA fragment was determined using M13 forward primer and M13 reverse primer (by the automated sequencer manufactured by Applied Biosystems, Inc., Model 370A).

As a result, the sequence of 336 bp corresponding to the nucleotide numbers 1 to 336 in SEQ. ID. No: 6 in the Sequence Listing has been determined. It has become clear that there are the 8th–16th amino acid (FVGDSMVQL) of SEQ. ID. No: 13 and the 1st–10th amino acid (IIVLGLLPRG) of SEQ. ID. No: 14, both clarified in Example 3, and this PCR reaction product is a part of the cDNA of the 30 kDa subunit of the oxidized phospholipid degrading enzyme.

(e) Cloning of cDNA of the 45 kDa subunit of the oxidized phospholipid degrading enzyme by MOPAC.

Using as a DNA template for a PCR reaction 5 ng of the cDNA obtained in step (b) (5), the cDNA was added with 5 µl of 10× PCR buffer, 8 µl of 1.25 mM dNTPs and 1 µl portions of 10 OD/ml primers (SEQ. ID. Nos: 26 and 27 to be described below). The total volume was then brought to 49 µl with DPC-treated distilled water. After the above solution was heated at 95° C. for 5 minutes, 0.25 µl of 5 U/ml TaqDNA polymerase (product of Perkin ElmerCetus Company) was added. A reaction cycle consisting of 1 minute at 94° C., 1 minute at 58° C. and 2 minutes at 72° C. was conducted 35 times, followed by incubation at 72° C. for 10 minutes. An analysis was then conducted by 2% agarose gel electrophoresis.

(SEQ. ID. No: 26)

GGNTA YGARG ARGCN TA (SEQ. ID. No: 27)

TGRTT NGGNC KNACC AT

A band of a PCR reaction product (660 bp) was observed by electrophoresis. After mineral oil was eliminated with chloroform, excess primers and dNTPs were removed using "Suprec TM02" (product of Takara Shuzo Co., Ltd.). A phenol-chloroform-isoamyl alcohol (25:24:1) solvent system was then added, followed by vigorous stirring. The resulting mixture was centrifuged at 14,000 g's for 10 minutes and 45 µl of the supernatant were transferred to a fresh centrifuge tube. The supernatant was added with 25 µl of 7.5M ammonium acetate and 150 µl of ethanol, stirred and then left over at –80° C. for 30 minutes. The mixture so obtained was centrifuged at 14,000 g's for 10 minutes. After the supernatant was decanted, the precipitate was washed with 0.5 ml of 70% ethanol, dried under reduced pressure and then dissolved in 5 µl of distilled water.

Subsequent to insertion into pCRII (product of Invitrogen Company), E. coll DH5α Max Efficiency component cells (product of BRL Company) were subjected to transformation. With respect to the plasmid DNA as the transformant, cloning was confirmed by PCR in which M13 reverse CAGGAAACAGCTATGAC (SEQ ID NO:30) and M13(- 20) forward GTAAAAC-GACGGCCAG (SEQ ID NO:31) were used. After the cloning, culture was conducted. The plasmid DNA was purified using CsCl and ultracentrifugation. The primary structural sequence of the inserted DNA fragment was determined using M13 forward primer and M13 reverse primer (by the automated sequencer manufactured by Applied Biosystems, Inc., Model 370A).

As a result, the sequence of 664 bp corresponding to the nucleotide numbers 1020 to 1683 in SEQ. ID. No: 8has been determined. It has become clear that there is the 1st–10th amino acid (TFTGHREWVR) of SEQ. ID. No: 17, clarified in Example 3, and this PCR reaction product is a part of the CDNA of the 45 kDa subunit of the oxidized phospholipid degrading enzyme.

Two types of oligomers (below-described SEQ. ID. Nos: 28 and 29) were synthesized based on the above found base sequence of the cDNA of the 45 kDa subunit.

(SEQ. ID. No: 28)

AAGAG ACCCA AAAGA ATG (SEQ. ID. No: 29)

GCACT TCCCA CATTT TTA

Using these oligomers, a full-length cDNA was cloned using PCR in accordance with the method reported by Kwiatkowski, Jr., T. J., Zoghbi, H. Y., Ledbetter, S. A., Ellison, K. A. and Chinault, A. C. in Nucleic Acids Res., 18, 7191–7192, 1990.

The cDNA plasmid library derived from bovine brain, said library having been prepared in step (b)(6), was placed on a 96-well plate by diluting it to distribute 50 clones per well. Stationary culture was then conducted overnight. Culture fluid were recovered by combining together, as a single pool, the fluid portions from the wells in each of 12 columns. Using 0.5 µl of the culture fluid as a DNA template for a PCR reaction, it was added with 5 µl of 10× PCR buffer, 8 µl of 1.25 mM dNTPs and 1 µl portions of the 10 OD/ml primers (SEQ. ID Nos. 29 and 30 described above). The total volume was brought to 49 µl with DPC-treated distilled water. After the mixture so obtained was heated at 95° C. for 5 minutes, 0.25 µl of 5 U/ml TaqDNA polymerase (product of Perkin Elmer Cetus Company) was added. A reaction cycle consisting of 1 minute at 94° C., 1 minute at 58° C. and 2 minutes at 72° C. was repeated 35 times, followed by incubation at 72° C. for 10 minutes. An analysis was then conducted by 2% agarose gel electrophoresis.

With respect to each pool on which a band of a PCR reaction product (400 bp) was observed by electrophoresis, a PCR reaction was conducted further. Each pool on which a band of the PCR reaction product (400 bp) was observed was lawned and each colony was subjected to a PCR reaction to achieve cloning. After the cloning, culture was conducted, and the plasmid DNA was purified using CsCl and ultracentrifugation. The primary structural sequence of the inserted DNA fragment was then determined (by the automated sequencer manufactured by Applied Biosystems, Inc., Model 370A).

The results are presented under SEQ. ID. No: 8 in the Sequence Listing. The coding initiator methionine was considered to be the 843rd nucleotide, and the 5'-untranslated region had 842 bp. The primary structural sequence of the cDNA of the 45 kDa subunit was determined. The number of amino acid residual groups in the structural gene was 410 and its estimated molecular mass was 46667.68 (including the coding initiator methionine). SEQ. ID. No: 16 was found at the amino acid numbers 2 to 28 in SEQ. ID. No: 8 in the Sequence Listing, SEQ. ID. No: 17 was found at the amino acid numbers 229 to 247 in SEQ. ID. No: 8 in the Sequence Listing, SEQ. ID. No: 18 was found at the amino acid numbers 375 to 390 in SEQ. ID. No: 8 in the Sequence Listing, and SEQ. ID. No: 19 was found at the amino acid numbers 406 to 410 in SEQ. ID. No: 8 in the Sequence Listing.

We claim:

1. An isolated enzyme that catalyzes the hydrolysis of oxidized phospholipids having the following physical and chemical properties:
   (A) the enzyme catalyzes hydrolysis of a 1,2-diacyl-3-phosphatidylcholine at the 2-ester position in which the 2-acyl group is an ω-carboxy fatty acid acyl group or an acetyl group to form a 1-acyl-2-lyso-3-phosphatidylcholine,
   (B) the enzyme has an optimal reaction pH of 7.0 to 8.0,
   (C) the enzyme catalyzed reaction is inhibited by 1 mM p-bromophenacyl bromide or 1 mM diisopropylfluorophosphate but is not inhibited by 1 mM iodoacetamide,
   (D) the enzyme activity is slightly enhanced by calcium ions as 4 mM calcium chloride,
   (E) the enzyme has a molecular mass of 95±5 kDa as determined by gel filtration,
   (F) the enzyme is composed of three subunits whose molecular masses have been found to be 29 kDa, 30 kDa, and 45 kDa, respectively by SDS-polyacrylamide gel electrophoresis.

2. An isolated enzyme that catalyzes the hydrolysis of oxidized phospholipids according to claim 1, which comprises a 29 kDa subunit having an amino acid sequence of SEQ ID NO:1.

3. An isolated enzyme that catalyzes the hydrolysis of oxidized phospholipids according to claims 1, which comprises a 30 kDa subunit having an amino acid sequence of SEQ ID NO:2.

4. An isolated enzyme that catalyzes the hydrolysis of oxidized phospholipids according to claim 1, which comprises a 45 kDa subunit having an amino acid sequence of SEQ ID NO:3.

5. An isolated polypeptide having an amino acid sequence of SEQ ID NO:1, and having a molecular mass of 29 kDa as determined by SDS-polyacrylamide gel electrophoresis.

6. An isolated mammalian enzyme that catalyzes the hydrolysis of oxidized phospholipids having the following physical and chemical properties:
   (A) the enzyme catalyzes hydrolysis of a 1,2-diacyl-3-phosphatidylcholine at the 2-ester position in which the 2-acyl group is an ω-carboxy fatty acid acyl group or an acetyl group to form a 1-acyl-2-lyso-3-phosphatidylcholine,
   (B) the enzyme has an optimal reaction pH of 7.0–8.0,
   (C) the enzyme catalyzed reaction is inhibited by 1 mM p-bromophenacyl bromide or 1 mM diisopropylfluorophosphate but is not inhibited by 1 mM iodoacetamide,
   (D) the enzyme activity is slightly enhanced by calcium ions as 4 mM calcium chloride,
   (E) the enzyme has a molecular mass of 95±5 kDa as determined by gel filtration,
   (F) the enzyme is composed of three subunits whose molecular masses have been found to be 29 kDa, 30 kDa, and 45 kDa, respectively by SDS-polyacrylamide gel electrophoresis.

7. An isolated mammalian enzyme that catalyzes the hydrolysis of oxidized phospholipids according to claim 6, which comprises a 29 kDa subunit having an amino acid sequence of SEQ ID NO:1.

8. An isolated mammalian enzyme that catalyzes the hydrolysis of oxidized phospholipids according to claim 6, which comprises a 30 kDa subunit having an amino acid sequence of SEQ ID NO:2.

9. An isolated mammalian enzyme that catalyzes the hydrolysis of oxidized phospholipids according to claim 6, which comprises a 45 kDa subunit having an amino acid sequence of SEQ ID NO:3.

* * * * *